United States Patent
Tursky et al.

(10) Patent No.: US 9,518,250 B2
(45) Date of Patent: Dec. 13, 2016

(54) METHOD FOR THE EX VIVO EXPANSION OF HEMATOPOIETIC STEM AND PROGENITOR CELLS

(71) Applicant: CYTOMATRIX PTY LTD, Geelong, Victoria (AU)

(72) Inventors: Melinda L. Tursky, Geelong (AU); Mark. A. Kirkland, Batesford (AU)

(73) Assignee: Nohla Therapeutics Australia Pty Ltd, Melbourne, Victoria (AU)

( * ) Notice: Subject to any disclaimer, the term of this patent is extended or adjusted under 35 U.S.C. 154(b) by 212 days.

(21) Appl. No.: 14/346,160

(22) PCT Filed: Sep. 21, 2012

(86) PCT No.: PCT/AU2012/001135
§ 371 (c)(1),
(2) Date: Mar. 20, 2014

(87) PCT Pub. No.: WO2013/040644
PCT Pub. Date: Mar. 28, 2013

(65) Prior Publication Data
US 2014/0286915 A1    Sep. 25, 2014

(30) Foreign Application Priority Data

Sep. 22, 2011   (AU) ................. 2011903899

(51) Int. Cl.
| A61K 38/00 | (2006.01) |
| C12N 5/18 | (2006.01) |
| C12N 5/0789 | (2010.01) |

(52) U.S. Cl.
CPC ....... *C12N 5/0647* (2013.01); *C12N 2501/125* (2013.01); *C12N 2501/145* (2013.01); *C12N 2501/22* (2013.01); *C12N 2501/2306* (2013.01); *C12N 2501/26* (2013.01); *C12N 2501/59* (2013.01); *C12N 2501/998* (2013.01)

(58) Field of Classification Search
None
See application file for complete search history.

(56) References Cited

U.S. PATENT DOCUMENTS

2002/0132017 A1    9/2002   Moore

FOREIGN PATENT DOCUMENTS

| CN | 101508975 A | 8/2009 |
| JP | 2008-237136 | 10/2008 |
| WO | 2004/089394 | 10/2004 |
| WO | 2005/007073 A3 | 1/2005 |
| WO | 2005/007799 A3 | 1/2005 |
| WO | 2006/045064 | 4/2006 |
| WO | 2007/066352 | 6/2007 |
| WO | 2008/149129 A1 | 12/2008 |
| WO | 2008/149129 A3 | 12/2008 |
| WO | 2010/142295 | 12/2010 |
| WO | 2011/030851 | 3/2011 |

OTHER PUBLICATIONS

The International Search Report of PCT/IL2004/000643 dated Jan. 12, 2005.
The International Search Report of PCT/IL2004/000644 dated Jan. 24, 2007.
Colucci G et al: "cDNA cloning of FRIL, a lectin from Dolichos lablab, that preserves hematopoietic progenitors in suspension culture", Proceedings of the National Academy of Sciences, National Academy of Sciences, US, vol. 96, Jan. 1, 1999, (Jan. 1, 199), pp. 646-650.
European Search Report for EP12832834, mailed Feb. 2, 2015.
Kogler, G. , et al 1998, "Volume reduction of cord blood by Hetastarch for long-term stem cell banking," Bone Marrow Transplant, Suppl 1:S14-5.
Sharma, S, et al., 2006, "Stem cell c-KIT and HOXB4 genes: critical roles and mechanisms in self-renewal, proliferation, and differentiation," Stem Cells Dev., 15(6):755-78.
Zhu, J. , et al., 2005, "NF-Ya activates multiple hematopoietic stem cell (HSC) regulatory genes and promotes HSC self-renewal," Proc Natl Acad Sci U S A,102(33):11728-33.
Stein, M.I., et al., 2004, "Molecular pathways regulating the self-renewal of hematopoietic stem cells," Exp Hematol., 32(12):1129-36.
Kogler, et al., 1998, "The effect if different thawing methods, growth factor combinations and media on the ex vivo expansion of umbilical cord blood primitive and committed progenitors," Bone Marrow Transplantation, 21:233-241.

*Primary Examiner* — Michail Belyavskyi
(74) *Attorney, Agent, or Firm* — McDonnell Boehnen Hulbert & Berghoff LLP

(57) ABSTRACT

The present invention relates to hematopoietic cells, and more specifically to methods for long-term in vitro culturing and ex vivo expansion of hematopoietic cells. The present invention also provides compositions useful for culturing cells, such as media for culturing hematopoietic cells, specifically haematopoietic stem cells (HSC) and haematopoietic progenitor cells (HPC). The present invention further provides compositions including growth factor combinations and methods utilizing altered growth and environmental conditions that are applicable in vitro culturing and to ex vivo expansion of HSC and/or HPC.

14 Claims, 14 Drawing Sheets

METHOD FOR THE EX VIVO EXPANSION OF HEMATOPOIETIC STEM AND PROGENITOR CELLS

FIELD OF THE INVENTION

The present invention relates to hematopoietic cells, and more specifically to methods for long-term in vitro culturing and ex vivo expansion of hematopoietic cells. The invention also provides compositions useful for culturing cells, such as media for culturing hematopoietic cells, specifically haematopoietic stem cells (HSC) and haematopoietic progenitor cells (HPC).

BACKGROUND OF THE INVENTION

Circulating blood cells, such as erythrocytes, leukocytes, platelets and lymphocytes, are the products of the terminal differentiation of recognisable precursor cells originating from hematopoietic progenitor cells (HPC) and hematopoietic stem cells (HSC).

The transplantation capability of hematopoietic cells in the treatment of haematological and immunological disorders and cancers has provided great benefits and advances in addressing the pathogenesis of many diseases. The expansion of HPC for bone marrow transplantation is one such example of the potential application of human long-term bone marrow cultures for use in treatment of disease.

Human autologous and allogeneic bone marrow transplantation are currently utilised as therapies for diseases such as leukemia, lymphoma, and other life-threatening diseases. For these procedures however a large amount of donor bone marrow must be removed to ensure that there are enough cells for engraftment for the treatment procedures. The ability to increase the number of hematopoietic cells such as HSC and HPC through expansion would reduce the need for large bone marrow donations and would make possible the ability to obtain a small marrow donation and then expand the number of progenitor cells in vitro prior to infusion into the recipient.

Human bone marrow cultures have been shown to present limited hematopoietic potential, producing decreasing numbers of hematopoietic progenitor and mature blood cells with cell production ceasing by six to eight weeks. This is largely attributed to the dependence of the HPC on various environmental influences, such as essential growth factors (hematopoietic growth factors and cytokines) found in vivo. In addition to these factors, interactions with cell surface molecules and extracellular matrices may be important for hematopoietic progenitor cell survival and proliferation. However, despite many efforts to advance in vitro expansion using exogenous growth factors, only a limited increase in the number of pluripotent cells has been successfully achieved.

Umbilical cord blood provides a source of HSC and HPC that can be manipulated and utilised for effective transplantation treatments of childhood diseases. These cells have shown a number of advantages over progenitor cells collected later in life, including a lower incidence of graft versus host disease (GvHD) and a greater tolerance of immunological incompatibility between donor and recipient.

The use of umbilical cord blood also provides a considerable advantage as a HSC source compared to bone marrow and mobilised peripheral blood, due to these cells' relative immunological and replicative immaturity that results in a lower incidence of GvHD, greater permissibility of human antigen leukocyte mismatches, and increased proliferative potential following transplantation. Disadvantages exist however as the use of umbilical cord blood for transplantation is limited in part to the low number of cells obtained per unit, and the delayed reconstitution of neutrophils and platelets. Further, the low numbers of HSC and HPC in each umbilical cord blood sample generally limit the sole usefulness of umbilical cord blood transplantation in full grown adult recipients.

There presently exist two main options for increasing the cell dose of HSC and HPC available for transplantation: either transfusion of multiple cord blood units, or ex vivo expansion. Dual umbilical cord blood has been used successfully in adult transplantation, resulting in reduced relapse and an increased potential for improved survival. However, dual transplantation utilising multiple cord blood units requires increased stringency in human antigen leukocyte (HLA) matching, and it is also associated with an increased incidence of GvHD. Additionally, as multiple cord blood transplantation does not affect cell composition, this option provides a limited ability to mitigate the delay in reconstitution. Due to these factors, interest has increased in ex vivo expansion for the generation of sufficient HSC and/or HPC for long-term engraftment, and to increase numbers of hematopoietic cells and multipotent cells capable of producing short-term reconstitution. The expanded cells can be transplanted alone, or with un-manipulated cells from the same or a different unit, to augment long-term engraftment while minimising reconstitutional delay.

Clinical trials have shown ex vivo expansion to be a safe and viable means of increasing cell dose, although it has initially been seen to produce only moderate expansion with a high degree of cell differentiation. More recently, it has been shown that significant expansion of HSCs and HPCs capable of repopulation is possible, but with no clear consensus regarding optimum expansion conditions. A method for expanding hematopoietic progenitor cells would therefore enhance the effectiveness of umbilical cord blood transplants and would also make hematopoietic cell sources like umbilical cord blood a viable source of HPCs for transplantation in adults.

The ability to more readily expand populations of HSCs and HPCs would also provide benefits in forming a supplemental treatment to chemotherapy, or provide assistance in the treatment of other disease states concerning an alteration of hematopoietic cells, and may also provide a further application for human long-term bone marrow cultures. A successful approach that can provide for HSC and HPC expansion would greatly facilitate the production of a large number of further differentiated precursor cells of a specific lineage, and in turn provide a larger number of differentiated hematopoietic cells with a wide variety of applications, including blood transfusions. This would greatly improve treatment aspects and outcomes of treatments such as chemotherapy.

A need therefore exists to provide systems, enhanced conditions, compositions and methods for the improved culture and maintenance of hematopoietic cells such as HSC and HPC to increase the cell dose available for transplantation and to influence favourably hematopoietic cell viability and pluripotency under long-term culture in vitro. Such an improvement is needed to also provide improved ex vivo expansion to lead to the generation of sufficient hematopoietic cells for long-term engraftment, and therefore to increase numbers of HPC and other multipotent cells capable of producing short-term reconstitution and to influence favourably hematopoietic progenitor cell viability and pluripotency under long-term culture in vitro.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

HSC manipulation is useful as a supplemental treatment to chemotherapy or radiation therapy. For example, HSC are localised into the peripheral blood and then isolated from a subject that will undergo chemotherapy, and after the therapy the cells are returned. Bone marrow is one of the most prolific tissues in the body and is therefore often the organ that is initially damaged by chemotherapy drugs and radiation. The result is that blood cell production is rapidly destroyed during chemotherapy or radiation treatment, and chemotherapy or radiation must be terminated to allow the hematopoietic system to replenish the blood cell supplies before a patient is re-treated with chemotherapy.

Accordingly, HSC and/or HPC transplantation is often used to treat haematological disorders and cancers such as multiple myeloma and leukaemia. HSC and HPC are commonly sourced from autologous bone marrow or a matched donor, however compatibility between the donor and recipient is often limiting. It is commonly difficult to locate a suitable and compatible donor, with only a 50% success rate of finding a matched donor in Caucasian patients. Further, the probability of finding a suitable donor decreases markedly in ethnic groups. Therefore, there presently exists a need to provide alternative sources of HSC and/or HPC to assist the treatment of those presently in need.

The present invention provides methods and compositions for extending the ex vivo viability of hematopoietic cells to increase their numbers while maintaining the properties of self-renewal and pluripotency. It is determined that through the culturing of a population of HPC and/or HSCs in the presence of any one of ficolin-1, ficolin-2, ficolin-3, or fragments or functional equivalents thereof, the ex vivo viability of a HPC and/or HSC population, or the culturing or expanding a HPC and/or HSC population can be extended Described herein are methods and compositions for enriching and expanding HSC and HPC ex vivo by growing cells in the presence of specific compositions and under particular culture conditions. Upon completion of cell culture based expansion of HSC and HPC, the cells can be isolated for further use such as in implantation, thereby reducing potential inflammatory reactions by increasing the number of HSC and HPC transplanted.

It is considered that the present invention can also provide novel compositions that utilise the effects of novel growth factor combinations as aforementioned and in combination with various culture conditions such as oxygen levels on HSC and/or HPC obtainable from numerous sources, such as from umbilical cord blood, so to increase the longevity of culture and pluripotency, multipotency, maintenance and/or expansion of these cells ex vivo. The present invention further provides for methods and products originating from the use of these methods whereby populations of HSC and/or HPC are further cultured in environments wherein the concentration of oxygen is less than a normal ambient oxygen concentration and which provides advantageous effects on the culture and the resulting cell populations.

The utilisation of various conditions and novel compounds on various target populations allows the selection of appropriate culture conditions for specific end-points defined by the resulting expanded cell type and the number of cells cultured and/or expanded prior to harvesting. As a result, optimised conditions have been identified for enhanced fold expansion of all target populations, with the potential for direct clinical translation to increase transplantable cell dose and minimise reconstitutional delay.

In addition, the present invention provides methods, expanded cell populations, populations of cells capable of being transplanted to a recipient in need thereof, devices and compositions for the controlled production in large numbers of specific lineages of progenitor cells and their more differentiated hematopoietic cells. In one embodiment of the invention, there is provided the controlled production and maintenance of the properties of self-renewal, pluripotency and differentiation result from conditions reminiscent of aspects of the hematopoietic niche, with optimisation of the effects of each factor separately and in combination.

Where the terms "comprise", "comprises", "comprised" or "comprising" are used in this specification (including the claims) they are to be interpreted as specifying the presence of the stated features, integers, steps or components, but not precluding the presence of one or more other features, integers, steps or components, or group thereof.

Other aspects of the present invention will become apparent to those ordinarily skilled in the art upon review of the following description of specific embodiments of the invention.

BRIEF DESCRIPTION OF THE FIGURES

For a further understanding of the aspects and advantages of the present invention, reference should be made to the following detailed description, taken in conjunction with the accompanying figures.

DETAILED DESCRIPTION OF THE INVENTION

Figure 1:
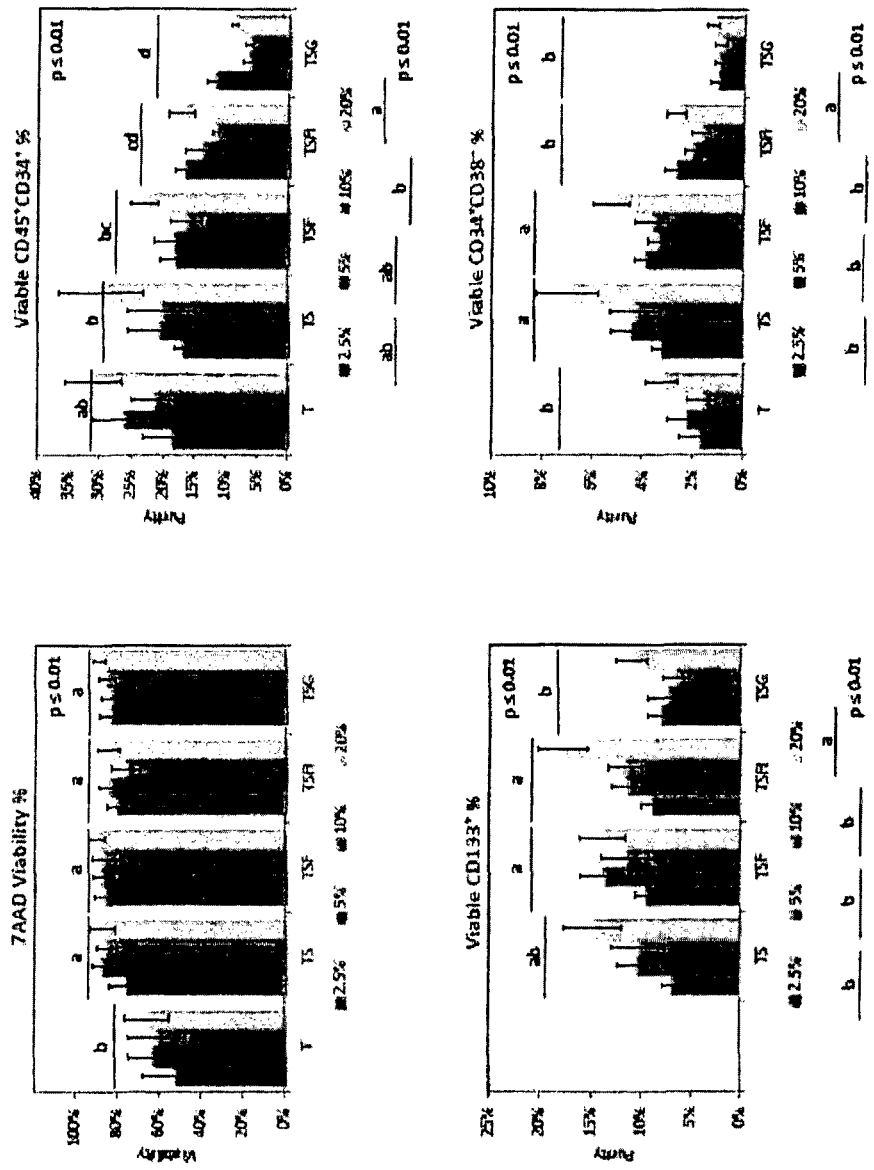
FIG. 1 shows the purity of target populations determined on the basis of cell surface markers or colony-forming units. $CD34^+$ enriched cells were incubated across a range of oxygen levels (2.5%≈19 mmHg, 5%≈38 mmHg, 10%≈75 mmHg, and 20%≈150 mmHg), in the presence of combinations of growth factors thrombopoietin (T, 50 ng/ml), stem cell factor (S, 50 ng/ml), Flt-3 ligand (F, 80 ng/ml) and Interleukin-6 (I, 100 ng/ml) (T, TS, TSF, TSFI), compared to thrombopoietin, stem cell factor and granulocyte colony-stimulating factor (TSG, each 100 ng/ml). Target populations were identified by flow cytometry using cell surface markers, and by growth in 'Complete' methylcellulose medium for enumeration of blast forming unit-erythrocyte (BFU-E), colony-forming unit-granulocyte/macrophage (CFU-GM), colony-forming unit-granulocyte/erythrocyte/monocyte/macrophage (CFU-GEMM), and total blast/colony-forming units. N=4 independent cord blood units, each performed in triplicate. Results are expressed as mean±standard error of the mean. Letters a-d indicate statistically different groups, with p values as shown.
Figure 1:
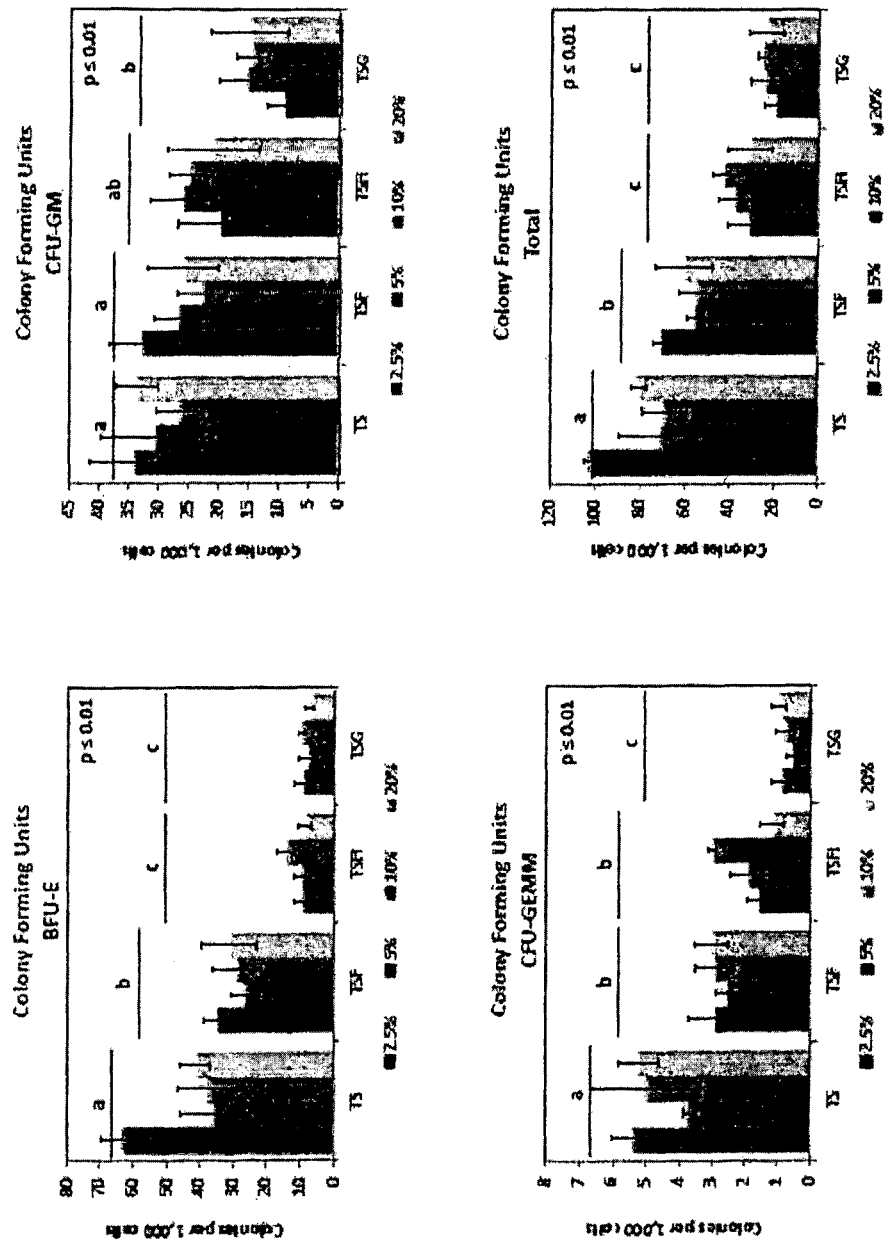

Human autologous and allogeneic bone marrow transplantation methods are used as therapies for diseases such as leukemia, multiple myeloma, lymphoma, and other life-threatening diseases. As such, in the treatment of haematological diseases, immunological disorders and cancers, HSC and HPC are turned to as an increasing more popular and established form of medical treatment.

Umbilical cord blood is often sought as a source for harvesting HSC and HPC where a compatible bone marrow donor for transplantation purposes is not available. Studies conducted in vitro have shown that HSC obtained from umbilical cord blood possess better proliferative and engraftment capability than those from bone marrow. Thus, the use of umbilical cord blood is considered to provide several advantages over other sources of hematopoietic cells, such as the fact that there is a less stringent requirement for matching the HLA in umbilical cord blood than in bone marrow. Unfortunately, the number of hematopoietic cells present and available in umbilical cord blood is often less than 0.1% of the total nucleated cells. The low population of these cells and the limited propensity for them to be successfully expanded to a suitable density for transplantation can often cause limitations and problems for their use, as the failure to achieve a threshold cell dose limit of, in some instances at least $1.7 \times 10^5$ CD34+ cells/kg, has been seen to correlate to a lower transplantation success rate.

A method of increasing stem cell numbers would furthermore reduce the time and discomfort associated with bone marrow/peripheral stem cell harvesting and subsequently increases the pool of stem cell donors. A method to increase stem cell numbers also permits umbilical cord blood to be useful for adult patients, thereby expanding the use of allogeneic transplantation.

Accordingly, the methods and compositions of the present invention provide improved systems and processes for the culturing, expansion and maintenance of hematopoietic cells. The present invention further provides for an improvement in the number of progeny that can be obtained from a sample of HPC or HSC while at the same time maintaining or increasing the repopulating capacity and pluripotency of those cells.

1. DEFINITIONS

The term hematopoietic stem cell, or "HSC" as used herein, refers to immature blood cells having the capacity to self-renew and to differentiate into more mature blood cells comprising granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), and monocytes (e.g., monocytes, macrophages). It is known in the art that such cells may or may not include CD34+ cells. CD34+ cells are immature cells that express the CD34 cell surface marker. CD34+ cells are believed to include a subpopulation of cells with the stem cell properties defined above.

It is also well known in the art that hematopoietic stem cells can include pluripotent stem cells, multipotent stem cells (e.g., a lymphoid stem cell), and/or stem cells committed to specific hematopoietic lineages. The stem cells committed to specific hematopoietic lineages may be of T cell lineage, B cell lineage, dendritic cell lineage, Langerhans cell lineage, erythroid, megakaryocytic, myeloid and/or macrophage cell lineage. In addition, HSCs also refer to long term HSC (LT-HSC) and short term HSC (ST-HSC). LT-HSC and ST-HSC are differentiated, for example, based on their cell surface marker expression. LT-HSC are CD34−, SCA-1+, Thy1.1+/lo, C-kit+, lin−, CD135−, Slamf1/CD150+, whereas ST-HSC are CD34+, SCA-1+, Thy1.1+/lo, C-kit+, lin−, CD135−, Slamf1/CD150+, Mac-1 (CD11b) lo ("lo" refers to low expression). In addition, ST-HSC are less quiescent (i.e., more active) and more proliferative than LT-HSC. However, LT-HSC have unlimited self-renewal (i.e., they survive throughout adulthood), whereas ST-HSC have limited self-renewal (i.e., they survive for only a limited period of time).

Any of these HSCs can be used in any of the methods described herein. Optionally, ST-HSCs are useful because they are highly proliferative and thus, quickly increase the number of HPSs and their progeny. Similarly, it is known in the art that such cells may or may not include CD133+ cells, which may also be found in the "blood products", and are also known to include a subpopulation of cells with the "progenitor cells" properties defined above. Additionally, HSCs are optionally obtained from blood products.

As considered in the present invention, the expanded HSCs retain at least some of the pluripotency of the initial stem cells or HSCs. Pluripotency includes stem cell activity or potential, such as the ability to differentiate into other blood cell types or the ability to multiply without differentiating.

A "blood product" as considered herein includes a product obtained from the body or an organ of the body containing cells of hematopoietic origin. Such sources include unfractionated bone marrow, umbilical cord, peripheral blood, liver, thymus, lymph and spleen. All of the aforementioned crude or unfractionated blood products can be enriched for cells having hematopoietic stem cell characteristics in a number of ways. For example, the more mature, differentiated cells are selected against, utilising cell surface molecules that they express. Optionally, the blood product is fractionated by selecting for CD34+ cells. CD34+ cells include a subpopulation of cells capable of self-renewal and pluripotentiality. Such selection is accomplished using, for example, commercially available magnetic anti-CD34 beads. Unfractionated blood products are optionally obtained directly from a donor or retrieved from cryopreservative storage. The ability to isolate HSC using specific stem cell markers are known to those skilled in the art.

According to the present invention, it is considered that all of the aforementioned crude or unfractionated blood products can be enriched for cells having hematopoietic progenitor cells, or "HPC" characteristics in a number of ways.

The term "HPC" as used herein refers to hematopoietic progenitor cells, which are rare in circulating blood, and are cells that can differentiate into a variety of specialised cell types, and give rise blood cells types. It is generally understood that they exist in the blood at various stages of maturation.

By way of a non-limiting example, the blood product can be depleted from the more differentiated progeny. The more mature, differentiated cells can be selected against cell surface molecules for which they posses and express. Specific ligands or receptors can also be utilised and the HPC can be enriched prior to further manipulation.

In the present invention it is considered that the term "ambient" relates to region that is completely surrounding or encompassing the present culture area. It is considered that the term ambient in the context used in the present specification would be understood by one of minimal skill in the art and that this term would be known by the skilled addressee.

The term "ambient concentration of oxygen" as used herein is understood to mean the amount of environmentally available oxygen found per unit volume in different environmental media or in the surrounding environment, and is considered to be a term that would be understood by a person skilled in the art.

The term "stromal cells" as used herein is considered to comprise fibroblasts and mesenchymal cells, with or without other cells and elements, and can be seeded prior to, or substantially at the same time as, the hematopoietic progenitor cells, therefore establishing conditions that favour the subsequent attachment and growth of HSC and/or HPC. Fibroblasts can be obtained via a biopsy from any tissue or organ, and include foetal fibroblasts. These fibroblasts and mesenchymal cells may be transfected with exogenous DNA that encodes, for example, one of the hematopoietic growth factors described.

According to the present invention, it is considered that the term "stromal cell conditioned medium" refers to medium in which the aforementioned stromal cells have been incubated. In the methods of the invention, the incubation is performed for a period sufficient to allow the stromal cells to secrete factors into the medium. Such "stromal cell conditioned medium" can then be used to supplement the culture of HPC promoting their proliferation and/or differentiation. Thus, when cells are cultured without any of the foregoing agents, it is meant herein that the cells are cultured without the addition of such agent except as may be present in serum, ordinary nutritive media or within the blood product isolate, unfractionated or fractionated, which contains the hematopoietic progenitor cells.

As considered in the present invention, the term "inoculated stromal cells" or "stromal cell inoculated medium" it is meant that the cell culture chamber is free of stromal cells which have been introduced into the chamber as an inoculum for promoting survival, proliferation or differentiation of the HPC, excluding, however, stromal cells which are contained naturally in the isolated blood product.

The "subject" as referred to herein is, for example, a bone marrow donor or an individual with or at risk for depleted or limited blood cell levels. Optionally, the subject is a bone marrow donor prior to bone marrow harvesting, or is a bone marrow donor after bone marrow harvesting. The subject is optionally a recipient of a bone marrow transplant. The methods described herein are particularly useful in subjects that have limited bone marrow reserve such as elderly subjects or subjects previously exposed to an immune depleting treatment such as chemotherapy. The subject, optionally, has a decreased blood cell level or is at risk for developing a decreased blood cell level as compared to a control blood cell level. As used herein the term control blood cell level refers to an average level of blood cells in a subject prior to or in the substantial absence of an event that changes blood cell levels in the subject. An event that changes blood cell levels in a subject includes, for example, anaemia, trauma, chemotherapy, bone marrow transplant and radiation therapy. For example, the subject has anaemia or blood loss due to, for example, trauma.

As considered in the present invention, the terms "harvesting hematopoietic stem cells", "harvesting hematopoietic progenitor cells", "harvesting HSC" or "harvesting HPC" are considered to refer to the dislodging or separation of cells and are considered as techniques to which the person skilled in the art would be aware. In one example, the "harvesting" may be accomplished through the use of a number of methods, such as enzymatic, non-enzymatic, centrifugal, electrical, or size-based methods, or preferably, by flushing the cells using culture media (e.g., media in which cells are incubated) or buffered solution. The cells are optionally collected, separated, and further expanded generating even larger populations of HSC or HPC and differentiated progeny.

As considered in the present invention, the term "control curve" is considered to refer to statistical and mathematically relevant curves generated through the measurement of the growth characteristics of different volumes of the blood product can be cultured under identical conditions, and wherein the cells can be harvested and counted over regular time intervals. These "control curves" as considered in the present invention can be used as one method to estimate cell numbers in subsequent occasions.

According to the methods of the present invention it is considered that any suitable expansion container, flask, or appropriate tube such as a 12, 24 or 96 well plate, 12.5 cm 2 T flask or gas-permeable bag can be used for any of the culturing methods of the present invention.\

As considered in the present invention, the term "hematopoietic growth factor" is considered to refer to at least one factor that influence the survival, proliferation or differentiation of hematopoietic cells. These growth factor(s) can be obtained by purification, by recombinant methodologies or can be derived or synthesised. Accordingly, the growth factor(s) that are of particular interest in connection with the methods and compositions of present invention are hematopoietic growth factors.

As considered in the present invention, the term "ficolin" is considered to relate to several variant proteins that exist in the ficolin family, including predominantly ficolin-1 (M-ficolin), -2, and -3. These are all secreted pattern-recognition lectins that contribute to the innate immune recognition of pathogens. Ficolins have one fibrinogen-like domain and one collagen-like domain and circulate as disulfide-linked homo-oligomers. Following ligand binding, ficolins associate with MASP serine proteases to trigger the lectin complement cascade. Ficolin-1 in humans is encoded by the FCN1 gene (SEQ ID: 1), ficolin-2 is encoded by the FCN2 gene (SEQ ID: 3), and ficolin-3 is encoded by the FCN3 gene (SEQ ID: 5). The protein products translated from FCN1, FCN2 and FCN3 are provided a SEQ ID: 2, SEQ ID: 4, and SEQ ID: 6 respectively.

Ficolins are proteins structurally related to the Angiopoietin-like proteins, and possess similar domain structures, particularly a single fibrinogen-like domain. In examination of the homology of ficolins and Angiopoietin-like proteins at the amino acid level, there is seen to be however only approximately 20-25% level of homology. The ficolin family of proteins are characterised by the presence of a leader peptide, a short N-terminal segment, followed by a collagen-like region, and a C-terminal fibrinogen-like domain. The collagen-like and the fibrinogen-like domains are also found separately in other proteins such as complement protein C1q, C-type lectins known as collectins, and tenascins. However, all these proteins recognise different targets, and are functionally distinct.

In all of the culturing methods according to the invention, except as otherwise provided, the media used can be one that is conventionally suitable for culturing cells. Examples of culture media known in the art and capable of being used for cell culture include RPMI, DMEM, ISCOVES. Typically these media are supplemented with human or animal plasma or serum. Such plasma or serum can contain small amounts of hematopoietic growth factors. In the preferred conditions of the present invention, the utilised media is provided without the addition of serum.

2. CULTURE OF HSC AND/OR HPC WITH FICOLIN

An ability to expand populations of HPC or HSC derived from a suitable source, such as umbilical cord blood or bone marrow, would provide substantial benefits to the medical community and improve prospects of successfully performing treatments, transplantation surgeries, or other therapies for hematologic and oncologic disease where higher cell doses are required.

In the present invention it has been discovered that the use of particular agents such as ficolins, when used either individually or in combination, can enhance the expansion of HSC and HPC populations. Ficolins are proteins structurally related to the Angiopoietin-like proteins, and possess similar domain structures, particularly a single fibrinogen-like domain. They have previously been recognised as modulators of immune function, however they have not been investigated for their effect on hematopoietic stem or hematopoietic progenitor cells.

These agents have been seen to provide enhancements to the self-renewal and expansion of hematopoietic cells. As discovered by the inventors (see Examples) it was found that maintenance of the most primitive class of colony forming cells, CFU-GEMM, was achievable in the presence, but not in the absence, of ficolins indicating that these agents are most likely active in selectively preserve primitive HSC populations.

Accordingly, in an aspect of the present invention there are provided supplements to cultures that are suitable for the growth of HSC and/or HPC, where the supplements provided are one or more of the agents ficolin-1, ficolin-2 or ficolin-3 or fragments or functional equivalents or combinations thereof.

As considered in the present invention, fragments and functional equivalents of ficolin are understood to include fragments that include the fibrinogen-like domain (in the case of ficolin 1, for example, amino acids 115-325), or smaller fragments that include the lectin-binding activity (as a non-limiting example), in the case of ficolin 1, amino acids 200-300).

In one embodiment, the population of hematopoietic cells for culture or expansion can be harvested, for example, from a bone marrow sample obtained from a suitable subject, from previously established culture, or from umbilical cord blood. Optionally, the HSC can be obtained from a blood product selected from the group comprising unfractionated bone marrow, umbilical cord, peripheral blood, liver, thymus, lymph and spleen.

In a further embodiment, the hematopoietic cell populations obtained from the use and application of the methods or compositions of the present invention can include HSC and/or HPC comprising an improved therapeutic potential due to their enhanced capacity to restore blood and immune cells in transplant recipients. In a yet another embodiment, it is considered that the cell populations cultured in accordance with the methods of the present invention can retain the potential to undergo differentiation in order to generate cells for other tissues such as for example, brain, muscle and liver cells.

It is considered that unfractionated blood products can be obtained directly from a donor or retrieved from cryopreservative storage, however it is viewed that these are merely non-limiting examples of where such blood products can be obtained in providing a source of hematopoietic cells for use in the methods of the present invention. According to the present invention, it is considered that the origin of hematopoietic cells from any suitable animal, for example, human, non-human primates, porcine or murine. In a preferred embodiment, the hematopoietic cells are human cells.

In an embodiment of the present invention, the methods for culturing the HSC and/or HPC as used in the present invention can utilise any of the growth factors as herein mentioned and can be supplemented with one or more of ficolin-1, ficolin-2 or ficolin-3 or fragments or functional equivalents or combinations thereof. In a preferred embodiment ficolin-1, ficolin-2, ficolin-3, fragments or functional equivalents or combinations thereof are added to in the culture system so to constitute between approximately 50 ng/mL-200 ng/mL of the culture media. In a more preferred embodiment the concentration of ficolin-1, ficolin-2, ficolin-3, fragments or functional equivalents or combinations thereof in the culture system are between approximately 50 ng/mL-100 ng/mL.

3. CULTURING OF HPC AND/OR HSC IN LOW OXYGEN ($O_2$) ENVIRONMENTS

In the present invention, the inventors have also determined that the amount of oxygen, when provided to a cell culture at levels less than the ambient concentration of oxygen can provide enhanced growth characteristics such as improved purity of target populations, with no or very limited effect on clonogenicity.

The effect of the low concentration of oxygen on the growth of cells such as HPC and/or HSC can be further attenuated through the inclusion of an agent such as ficolin, or functional equivalents thereof, whereby there is provided improved purity of target populations, with minimal effect on clonogenicity.

Accordingly, in a further aspect of the present invention there are provided methods for extending ex vivo viability of a HPC and/or HSC population, or culturing or expanding a HPC and/or HSC population, where said method comprising culturing the HPC and/or HSC population in the presence of ficolin-1, ficolin-2 or ficolin-3 or fragments or functional equivalents or combinations thereof and in an environment wherein the concentration of oxygen is reduced compared with the normal ambient oxygen concentration.

The culture of the hematopoietic cells preferably occurs under conditions to increase the number of such cells and/or the colony forming potential of such cells. The conditions used refer to a combination of conditions known in the art (e.g., temperature, $CO_2$ content, nutritive media, etc.). In particular however, the inventors have found that the concentration of oxygen in the culture environment is critical to the expansion of hematopoietic progenitor cells.

In an embodiment of the invention, the population of HSC and/or HPC of the present invention can be cultured in a low oxygen environment to enhance their probability of self-renewal and decrease the probability of differentiation and do so in the presence of an agent such as ficolin-1, ficolin-2 or ficolin-3 or fragments or functional equivalents or combinations thereof.

In a further embodiment, there are provided methods for modifying the capacity to extend ex vivo viability of a population of HPC and/or HSC, or culturing or expanding a HPC and/or HSC population through the appropriate selection of oxygen concentrations during culture, and where an agent such as ficolin-1, ficolin-2 or ficolin-3 or fragments or functional equivalents or combinations thereof have been provided to the culture system.

In another embodiment, the concentration of oxygen in the culture system constitutes less than the ambient concentration level of oxygen present in the atmosphere. In a more preferred embodiment, the concentration of oxygen is less than approximately 20%, more preferably the oxygen is between approximately 1% and approximately 12% of the culture atmosphere. In a particularly preferred embodiment oxygen constitutes approximately 10% of the culture atmosphere.

In a further embodiment, the cells of the present invention are cultured in the presence of an agent such as ficolin-1, ficolin-2 or ficolin-3 or fragments or functional equivalents thereof and in an environment wherein the concentration of oxygen is less than the ambient level of oxygen present in the environment and where the cells are cultured in an oxygen concentration of between approximately 1% and approximately 12% oxygen.

In another embodiment, the cells of the present invention are cultured in the presence of any one or more agents such as ficolin-1, ficolin-2 or ficolin-3 or fragments or functional equivalents, in an environment wherein the concentration of oxygen is at least 0.5%, or at least 1.0%, or at least 1.5%, or at least 2.0%, or at least 2.5%, or at least 3.0%, or at least 3.5%, or at least 4.0%, or at least 4.5%, or at least 5.0%, or at least 5.5%, or at least 6.0%, or at least 6.5%, or at least 7.0%, or at least 7.5%, or at least 8.0%, or at least 8.5%, or at least 9.0%, or at least 9.5%, or at least 10.0%, or at least 10.5%, or at least 11.0%, or at least 11.5%, or at least 12.0%, or at least 12.5%, or at least 13.0%, or at least 13.5%, or at least 14.0%, or at least 14.5%, or at least 15.0%, or at least 15.5%, or at least 16.0%, or at least 16.5%, or at least 17.0%, or at least 17.5%, or at least 18.0%, or at least 18.5%, or at least 19.0%, or at least 19.5%, or at least 20.0%.

In a preferred embodiment, an oxygen concentration in the range of 5-10% may be used in the culture of umbilical cord blood HSC and/or HPC in the presence of an agent such as any one or more of ficolin-1, ficolin-2 or ficolin-3 or fragments or functional equivalents or combinations thereof. In particularly preferred embodiment, an oxygen concentration of approximately 5% may be used in the culture of HSC and/or HPC.

In accordance with the methods of the present invention, it is considered that the time necessary to culture and expand populations of HSC and/or HPC in accordance with the methods and using the compositions of the present invention and under reduced oxygen, is a time that can be determined by a person skilled in the art. This can be understood to vary depending upon the original number of cells seeded during culture. As a non-limiting example, discoloration of the media can be used as an indicator of confluency.

It is further considered that in the application of the embodiments of the present invention, different volumes of a blood product can be cultured under identical conditions in order to generate "control curves" that can be used to estimate cell numbers in subsequent occasions. It is considered that the art, and therefore one of ordinary skill, is replete with techniques to determine the appropriate culture time using the modified oxygen concentration conditions and methods of the present invention. As may be contemplated by one of ordinary skill, various factors may however affect the measurement or time span encountered in the culture of cells. Considerations such as the initial seeding density at culture may affect the culture time. For example, if more cells are seeded initially, the optimum time for culture may be shortened relative to if a lesser number of cells were initially provided for seeding.

It would be considered however that the application of techniques such as in monitoring for a change in cell number (for example, by determining optical density or direct counting), by monitoring for changes in pH of the media, or examining for a slowing of rate of growth (for example, by calculating the doubling time of the cells) may all represent valid and suitable means for determining the appropriate culture time.

In a further embodiment of the present invention, ficolin-1, ficolin-2 or ficolin-3 or fragments or functional equivalents or combinations thereof are provided in addition to culture media suitable for growth of HPC and/or HSC, where the culture conditions include oxygen concentrations at less than the ambient level, and more preferably less than approximately 15%, less than approximately 14%, less than approximately 13%, less than approximately 12%, less than approximately 11%, less than approximately 10%, less than approximately 9%, less than approximately 8% less than approximately 7%, less than approximately 6%, or less than approximately 5%.

In a preferred embodiment, ficolin-1, ficolin-2 or ficolin-3 or fragments or functional equivalents or combinations thereof are provided to culture media wherein the oxygen concentration is approximately 5%. In a particularly preferred embodiment, ficolin-1 or fragments or functional equivalents thereof are provided in addition to the culture media wherein the oxygen concentration is approximately 5%.

4. CULTURING OF HSC AND/OR HPC WITH FICOLIN USING ALTERED CULTURE CONDITIONS

The expansion of hematopoietic cell populations such as HSC and/or HPC in vivo is a function of the combined influence of multiple factors within the bone marrow environment within which these cells are normally found. This area is quite commonly termed the "hematopoietic niche".

The most primitive and pluripotent stem cells are usually located immediately adjacent to the endosteal surface within the trabecular spaces in the bone marrow. This niche is therefore composed of cellular interactions between the stem cells and adjacent stromal cells, including osteoblasts, as well as interactions with extracellular matrix components, three dimensional interrelationships between different cell types, and the diffusion of growth factors and other soluble signal molecules within the bone marrow cavity.

Accordingly, in a further aspect of the present invention, there are provided methods for the culture of HSC and/or HPC in the presence of agents such as ficolin-1, ficolin-2 or ficolin-3 or fragments or functional equivalents or combinations thereof, and additionally in the presence of growth factors as herein described which can provide additional effects to the culture of the cells, such as an increase in the renewal and pluripotency properties of the HSC and/or HPC cells.

In utilising the methods of the present invention it is possible to take an enriched population of HSC and/or HPC, and stimulate them with agents and/or growth factors that promote hematopoietic cell maintenance, or promote expansion and/or differentiation in order to yield the more mature blood cells, in vitro. Such expanded populations of blood cells may be applied in vivo, such as in replenishing a patient's hematopoietic cell population, or may be used experimentally. Such differentiated cells include those described above, as well as T cells, plasma cells, erythrocytes, megakaryocytes, basophils, polymorphonuclear leukocytes, monocytes, macrophages, eosinophils and platelets.

The growth factors that are of particular interest in connection with the methods and compositions of the present invention are hematopoietic growth factors. These growth factors can be obtained by purification, by recombinant methodologies or can be derived or synthetically.

In an embodiment of the present invention there are provided methods for culturing or expanding HSC and/or HPC populations in conventional growth media in the presence of ficolin-1, ficolin-2 or ficolin-3 or fragments or functional equivalents or combinations thereof, with the addition of a growth factor selected from the group comprising interleukins 3, 6 and 11 (I), stem cell factor (S), thrombopoietin (T), fibroblast growth factor, insulin-like growth factor and FLT-3 ligand (F).

As determined by the inventors of the present invention, and as discussed in the Examples, thrombopoietin alone resulted in cell viability of only 60% and which is below preferred transplant standards and unsuitable for maintenance of cell cultures for research. The combination of growth factors TS when provided to the culture media was seen to increase the viability of expanded cells. In addition, TS increased the percentage of the most primitive HSC (CD34$^+$CD38$^{--}$) to levels higher than were observed pre-culture, and dramatically increased fold expansion.

Accordingly, in a further embodiment of the present invention, the growth factors TS are provided to a culture media comprising HPC and/or HSC and ficolin-1, ficolin-2 or ficolin-3 or fragments or functional equivalents thereof to increase the viability of the expanded culture.

In a further embodiment, populations of HPC and/or HSC can be cultured with a combination of growth factors where the culture can comprise thrombopoietin (T), stem cell factor (S), FLT-3 ligand (F) and Interleukin-6 (I) in the culture media. In a further embodiment of the present invention, the agents ficolin-1, ficolin-2 or ficolin-3 or fragments or functional equivalents or combinations thereof are provided in addition to the growth factor combination of TSFI.

In still a further embodiment of the present invention, each growth factor can be provided at a concentration in the range of approximately 50 ng/mL-100 ng/mL. In preferred embodiment, in the application of the methods or compositions of the present invention, T is provided at approximately 50 ng/mL, S is provided at approximately 50 ng/mL, F is provided at approximately 80 ng/mL, and is provided at approximately 100 ng/mL.

As also determined by the inventors, the addition of Flt-3 ligand (F) to the combination TS has minimal additive effects on purity and fold expansion of most target populations, although there was determined to be a significant reduction in BFU-E and CFU-GEMM clonogenicity. Therefore, in a further embodiment there is provided the growth factor F in combination with TS in the presence of HSC and/or HPC for the culture of the aforementioned cells.

In the application of the methods of the present invention, the addition of interlukin-6 (I) was observed to decrease the overall purity and clonogenicity of target populations with TSFI when compared to TS or TSF, but this combination also showed a dramatic increase in viable cell fold expansion with a corresponding increase in clinically predictive populations of $CD45^+CD34^+$ and $CD133^+$, and the more primitive $CD34^+CD38^{--}$ population.

Together with the increase in $CD34^+CD38^{--}$ expansion, the inventors have also determined that interleukin-6 in combination with other growth factors can influence cord blood HSC fate. The combination TSFI significantly increased fold expansion of CFU-GM, CFU-GEMM and total blast/colony-forming units, indicative of a greater short-term repopulating capacity. In contrast, the growth factor combination TS and granulocyte-colony stimulating factor (G) (i.e. TSG) resulted in similar fold-expansion of viable cells, but a much higher proportion of differentiated cells. This shift towards granulocytic differentiation at the expense of expansion of other stem and progenitor populations may result in exhaustion of the most primitive HSC with less beneficial outcomes after transplantation.

It is considered that through the utilisation of the methods and compositions of the present invention, it is possible that the culture of HSC, such as HPC can be performed for 6, 7 or 8 weeks, and that it is possible to harvest hematopoietic progenitor cells during this time interval for subsequent exposure to culture conditions containing hematopoietic growth factors that promote hematopoietic cell maintenance, expansion and/or differentiation.

Accordingly, in a further embodiment, the growth factors TSFI are provided to a culture media for culturing HSC and/or HPC so to increase the period to which the aforementioned cells can be cultured. Preferably, they may be cultured to a period of 6 weeks, more preferably a period of 7 weeks, and even more preferably a period of 8 weeks. In a further embodiment of the present invention, agents such as ficolin-1, ficolin-2 or ficolin-3 or fragments or functional equivalents or combinations thereof are provided in addition to the growth factor combination of TSFI.

5. CULTURE OF HSC AND/OR HPC IN CONDITIONS OF SELECTED CULTURE MEDIA WITH FICOLIN AND LOW OXYGEN

In a further aspect of the present invention, there are provided methods and compositions for the culture HSC and/or HPC in a low oxygen environment and in the presence growth factors and agents such as ficolin-1, ficolin-2 or ficolin-3 or fragments or functional equivalents or combinations thereof, and in the presence of reduced oxygen concentrations compared to the ambient level.

In one embodiment, there is provided the growth factor combination of TSFI at any of the aforementioned concentrations and combinations in the culture media, and the presence of any one of ficolin-1, ficolin-2 or ficolin-3 or fragments or functional equivalents or combinations thereof and in an environment where the oxygen concentration is less than the ambient concentration of oxygen. In a preferred embodiment, the concentration of oxygen is less than 20%. In a more preferred embodiment, there is provided the growth factor combination of TSFI present wherein the oxygen levels of 5%-10% which results in enhanced fold expansion of all target populations. In a particularly preferred embodiment there is provided the growth factor combination of TSFI in the presence of an oxygen level of 10% which can provide enhanced fold expansion of all target HSC/HPC populations.

Through the application of the methods and compositions of the present invention it has been shown that a growth factor combination of TSFI at oxygen levels of 5% and 10% results in enhanced fold expansion of all target populations, and therefore represents the most desired conditions for increasing transplantable cell doses from umbilical cord blood.

It has also been determined by the inventors that in the use of the methods and compositions as hereinbefore described, that if HSC and/or HPC are cultured in the presence of a growth factor combination such as TS±F, an effect is that there is provided an enhancement in the probability of self-renewal of these cells and therefore to decrease the probability of differentiation.

In a further embodiment of the present invention, the hematopoietic cells of the present invention can be cultured in the presence of a growth factor combination TS±F and in the presence of ambient oxygen levels to provide a maximisation of purity. In a more preferred embodiment oxygen constitutes approximately 20% of the culture atmosphere in the presence of the growth factor combination TS±F. In an further preferred embodiment, there is provided a growth factor combination TS±F in an approximately 20% oxygen level to provide expansion while maximising purity for increasing purity of a primitive $CD34^+CD38^-$HSC population.

In a further aspect of the present invention, methods are provided for the culture of HSC and/or HPC where they can be cultured in a low oxygen environment in combination with an agent such as ficolin, optimised growth factors of TSFI to enhance their probability of self-renewal and decrease the probability of differentiation. In one embodiment, oxygen in the culture system constitutes 1%, 2%, 3%, 4%, 5%, 6%, 7%, 8%, 9%, 10%, 11%, 12%, 13%, 14% and 15% of the culture atmosphere in the presence of growth factors TSFI. In another embodiment, the oxygen concentration constitutes approximately 10% of the culture atmosphere in the presence of growth factors TSFI. In yet another embodiment the oxygen concentration constitutes approximately 10% of the culture atmosphere in the presence of growth factors TSFI. In a particularly preferred embodiment, the oxygen concentration constitutes approximately 5%.

In another embodiment, ficolin-1, ficolin-2 or ficolin-3 or fragments or functional equivalents thereof are provided in addition to the growth factor combination of TSFI where the oxygen concentration is less than the ambient level, and more preferably less than approximately 10%, less than approximately 9%, less than approximately 8% less than approximately 7%, less than approximately 6%, or less than approximately 5%.

In a preferred embodiment, ficolin-1, ficolin-2 or ficolin-3 or fragments or functional equivalents or combinations thereof are provided in addition to the growth factor combination of TSFI wherein the oxygen concentration is approximately 5%.

In a particularly preferred embodiment, ficolin-1 or fragments or functional equivalents thereof are provided in addition to the growth factor combination of TSFI wherein the oxygen concentration is approximately 5%.

6. COMPOSITIONS FOR THE CULTURE OF HSC AND/OR HPC WITH SELECTED MEDIA

As previously discussed, the growth factors that are of particular interest in connection with the methods and compositions of the present invention are hematopoietic growth factors. Accordingly, a further aspect of the present invention is directed toward providing culture compositions for extending ex vivo viability of a HPC and/or HSC population, or culturing or expanding HSC and/or HPC populations in conventional growth media for use in the methods of the present invention.

In an embodiment of the present invention, there are provided compositions that can include ficolin-1, ficolin-2 or ficolin-3 or fragments or functional equivalents or combinations thereof. In a preferred embodiment ficolin-1, ficolin-2, ficolin-3, fragments or functional equivalents or combinations thereof are added to in the culture system so to constitute between 50 ng/mL-200 ng/mL of the culture media. In a preferred embodiment the concentration of ficolin-1, ficolin-2, ficolin-3, fragments or functional equivalents or combinations thereof in the culture system are between approximately 50 ng/mL-200 ng/mL. In a more preferred embodiment, the concentration of ficolin-1, ficolin-2, ficolin-3, fragments or functional equivalents or combinations thereof in the culture system are between approximately 50 ng/mL-100 ng/mL.

In a particularly preferred embodiment, the concentration of ficolin-1, ficolin-2, ficolin-3, fragments or functional equivalents or combinations thereof in the culture system are provided at approximately 50 ng/mL, or at approximately 51 ng/mL, or at approximately 52 ng/mL, or at approximately 53 ng/mL, or at approximately 54 ng/mL, or at approximately 55 ng/mL, or at approximately 56 ng/mL, or at approximately 57 ng/mL, or at approximately 58 ng/mL, or at approximately 59 ng/mL, or at approximately 60 ng/mL, or at approximately 61 ng/mL, or at approximately 62 ng/mL, or at approximately 63 ng/mL, or at approximately 64 ng/mL, or at approximately 65 ng/mL, or at approximately 66 ng/mL, or at approximately 67 ng/mL, or at approximately 68 ng/mL, or at approximately 69 ng/mL, or at approximately 70 ng/mL, or at approximately 71 ng/mL, or at approximately 72 ng/mL, or at approximately 73 ng/mL, or at approximately 74 ng/mL, or at approximately 75 ng/mL, or at approximately 76 ng/mL, or at approximately 77 ng/mL, or at approximately 78 ng/mL, or at approximately 79 ng/mL, or at approximately 80 ng/mL, or at approximately 81 ng/mL, or at approximately 82 ng/mL, or at approximately 83 ng/mL, or at approximately 84 ng/mL, or at approximately 85 ng/mL, or at approximately 86 ng/mL, or at approximately 87 ng/mL, or at approximately 88 ng/mL, or at approximately 89 ng/mL, or at approximately 90 ng/mL, or at approximately 91 ng/mL, or at approximately 92 ng/mL, or at approximately 93 ng/mL, or at approximately 94 ng/mL, or at approximately 95 ng/mL, or at approximately 96 ng/mL, or at approximately 97 ng/mL, or at approximately 98 ng/mL, or at approximately 99 ng/mL, or at approximately 100 ng/mL.

In yet a further embodiment, there can additionally be included growth factor(s) selected from the group comprising interleukins 3, 6 and 11 (I), stem cell factor (S), thrombopoietin (T), fibroblast growth factor, insulin-like growth factor and FLT-3 ligand (F).

In another embodiment of the present invention, each growth factor is provided at a concentration of 50 ng/mL-100 ng/mL. In a more preferred embodiment, T is provided at approximately 50 ng/mL, S is provided at approximately 50 ng/mL, F is provided at approximately 80 ng/mL, and I Is provided at approximately 100 ng/mL. In a further embodiment, a combination of growth factors are cultured with the HPC and/or HSC when the culture comprises thrombopoietin (T), stem cell factor (S), FLT-3 ligand (F) and Interleukin-6 (I) in the culture media.

7. CULTURING METHODS OF HSC/HPC WITH SELECTED MEDIA COMPOSITIONS

In a further aspect of the invention, there are provided methods for in vitro culture of HSC and/or HPC, to produce differentiated cells of hematopoietic origin wherein in a first culturing step, a first amount of hematopoietic progenitor cells is expanded in an environment under conditions and for a period of time to increase the number of cultured hematopoietic progenitor cells relative to said first amount or to increase the number of the hematopoietic progenitor cells, thereby producing a second amount of hematopoietic progenitor cells. The time required to increase the number of cultured hematopoietic progenitor cells is can be determined by measurements known to practitioners of the art, such as measurement of cell number, optical density or pH of the culture, or by calculating the doubling time of the cells.

In a second culturing step, at least a portion of the second amount of cultured hematopoietic cells, such as hematopoietic progenitor cells, are cultured in an environment that includes at least one agent selected from the group consisting of a hematopoietic growth factor as discussed above that promotes hematopoietic cell maintenance, expansion and/or differentiation, inoculated stromal cells and stromal cell conditioned medium, to produce differentiated cells of hematopoietic origin.

In application of the methods of the present invention, the culturing can further comprise a second culturing step that can be a plurality of second culturing steps, each comprising culturing only a portion of a second amount of hematopoietic cells, such as HPC.

In a further aspect of the present invention, the hematopoietic progenitor cells are continuously cultured for an extended period of time, and aliquots of the cultured cells are harvested spaced apart in time or intermittently. In an embodiment of the present invention, the cells are suspended in media containing growth factors and other agents as herein described, and the cells can be harvested simply by agitation and centrifugation of the media. Therefore, in an embodiment of the present invention it is possible to expand the number of hematopoietic progenitor cells, and simultaneously harvest portions of those cells being expanded for treatment to develop even larger populations of differentiated cells.

The present invention is considered to bring together many different aspects of the hematopoietic niche, including optimisation of growth factor types and concentrations to maximise hematopoietic self-renewal, addition of other novel and known factors, and optimisation of culture conditions and systems. The sum of these aspects represents a novel and effective system for increasing the number of HSC capable of repopulating tissues and organs such as the bone marrow after transplantation.

The isolated cell population provided using the methods of the present invention will have an enriched population of cells compared with a naturally occurring cell population. Typically, the cell population is a HSC or HPC cell population, selectively enriched from a biological source. The cell populations may comprise enriched populations of HSC and/or HPC CD34+CD38− or CD133+CD38− cells.

8. USE OF HSC AND/OR HPC CULTURED ACCORDING TO THE METHODS OF THE PRESENT INVENTION FOR TRANSPLANTATION OR THERAPY

In a further aspect of the present invention, the hematopoietic cells cultured according to the methods of the present invention can be utilised for bone marrow transplantation of a subject.

The potential application of hematopoietic cells cultured according to the methods of the present invention can be envisaged to supplement or replace human autologous and allogeneic bone marrow transplantation currently used as therapies for diseases such as leukemia, lymphoma, and other life-threatening diseases.

In a further aspect of the present invention, there are also provided methods of treating an individual in need of a hematopoietic stem cell-based therapy, comprising removing hematopoietic stem cells from the individual or from a donor; culturing the cells in a culture medium containing an amount of growth factor combination as considered herein, a protein effective to promote expansion of hematopoietic stem cells, such as any of the aforementioned ficolin proteins, harvesting the cultured cells, and transplanting the cultured cells into the individual.

The HSC produced by the methods of the present invention can be provided to the subject, for example, before, at the same time, or after chemotherapy, radiation therapy or a bone marrow transplant. The subject optionally has depleted bone marrow related to, for example, congenital, genetic or acquired syndrome characterised by bone marrow loss or depleted bone marrow. Thus, the subject is optionally a subject in need of hematopoeisis. Optionally, the subject is a bone marrow donor or is a subject with or at risk for depleted bone marrow.

Employing the methods and conditions of the present invention, it is possible to increase the period of time of culture of HPC and to stimulate the expansion of HPC number and/or colony forming unit potential. In one embodiment, it is considered that once expanded, the cells, for example, can be returned to the body to supplement or replenish a patient's hematopoietic progenitor cell population. This can be advantageous, in the instance following a period where an individual has undergone chemotherapy. Furthermore, there are certain genetic conditions such as thalassemias, sickle cell anemia, Dyskeratosis congenital, Shwachman-Diamond syndrome, and Diamond-Blackfan anemia wherein HPC numbers are decreased, and the methods of the invention in expanding HSC and/or HPC number may be useful and applicable.

The present invention will now be more fully described by reference to the following non-limiting Examples.

EXAMPLES

Example 1

CD34+ Cell Enrichment

Umbilical cord blood was collected from full-term deliveries at Barwon Health, Geelong Hospital and St. John of God Hospital Geelong, Australia, under approval from Barwon Health Human Research Ethics Committee (97/14 and SJOG 139) and Deakin University Human Research Ethic Committee (EC 72-2009), with all participants providing written informed consent.

Within 24 hours of collection, mononuclear cells were obtained by Ficoll-paque Plus (GE Healthcare) density gradient centrifugation, followed by CD34+ cell enrichment using direct antibody-labelled magnetic bead kit and dual columns (Miltenyi Biotec). A cell aliquot was used for flow cytometric analysis, and the remainder cryopreserved in Recovery Freezing Media (Invitrogen).

Figure 4:
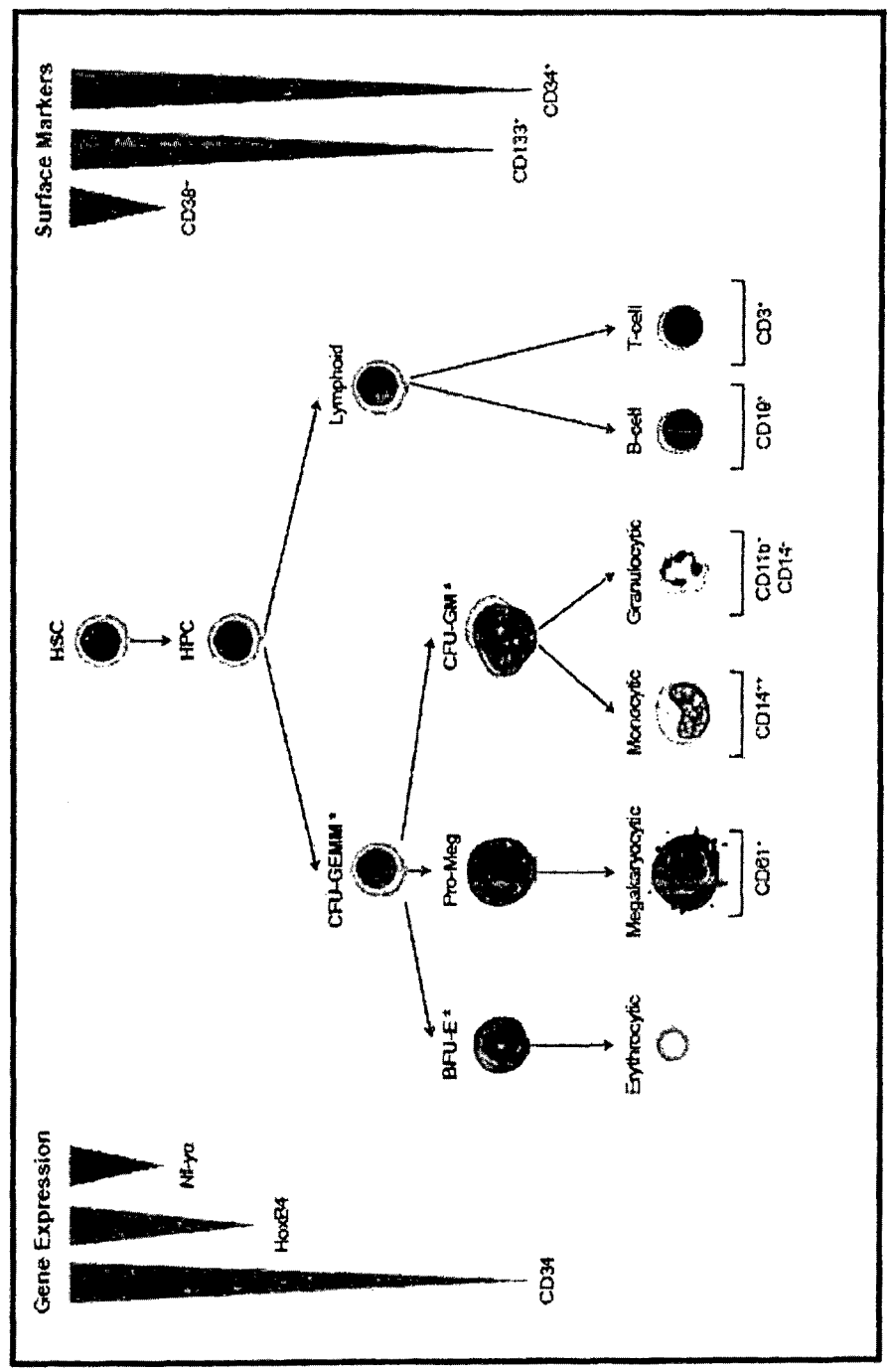
FIG. 4 shows Hematopoietic cell types that were distinguishable utilising three methods of assessment. 1) Expression patterns of surface marker cluster of differentiation molecules (CD) for phenotypic identification of stem, progenitor and multipotent cells, as indicated on the right hand side, and for lineage committed cells as indicated below. 2) Functional assessment of multipotent cells were performed with Colony/Blast Forming Unit (CFU/BFU) assays for granulocyte (G), erythrocyte (E), monocyte (M) and macrophage (M) cells, as indicated (*). 3) Gene expression patterns for self-renewing hematopoietic stem cells, and for progenitor and multipotent cells are indicated on the left hand side. (Cell images adapted from A. Rad, 2007.)
Figure 5:
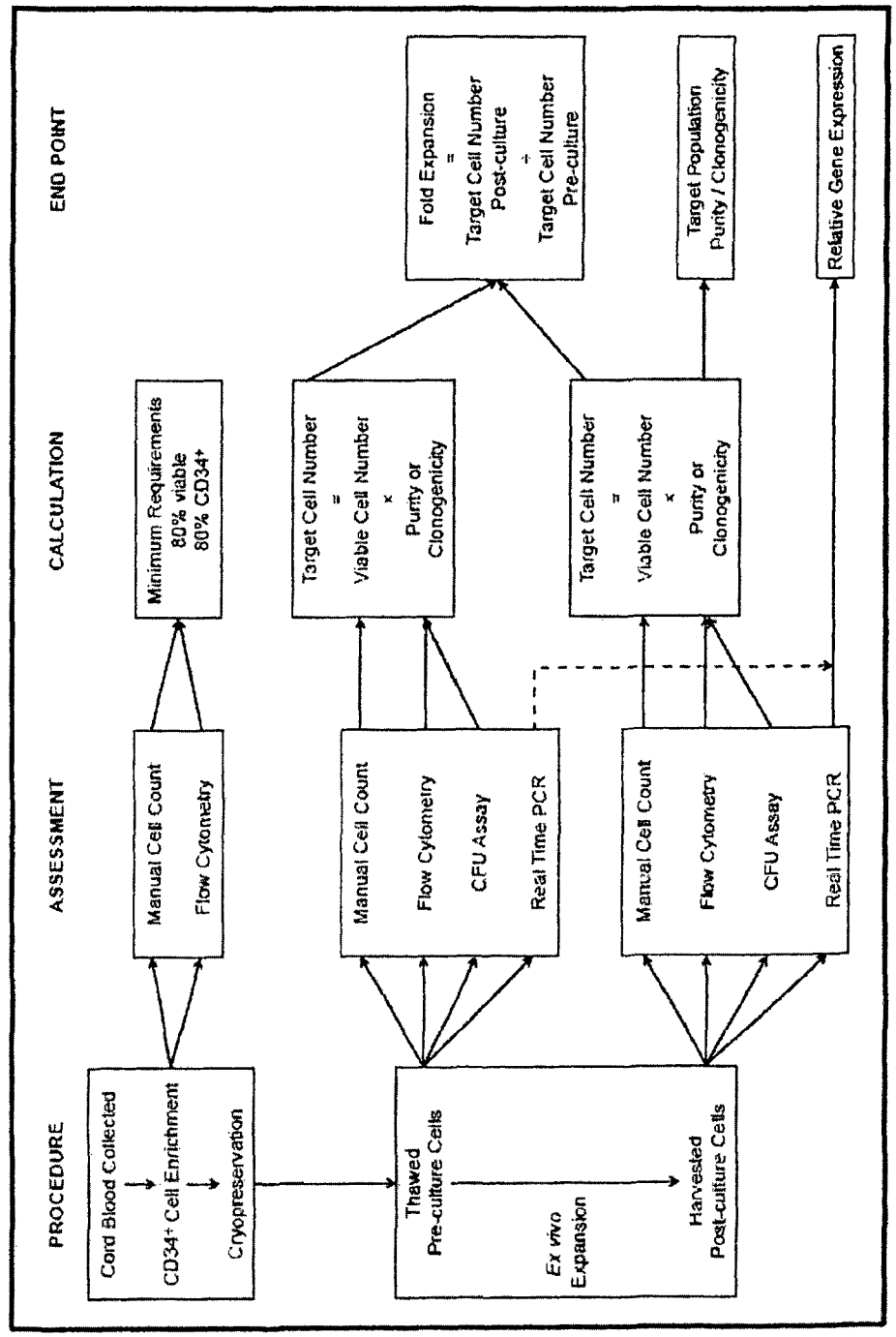
FIG. 5 shows that after CD34+ enrichment, only samples with a viability and CD34+ purity of 80% or greater were used for ex vivo expansion. Cells were assessed both pre- and post-culture for single step and serial expansion. Viable cell number was determined by manual count with trypan blue exclusion. Purity of target populations was determined as a percentage of cells expressing surface marker combinations by flow cytometry, and clonogenicity as the number of blast or colony-forming units per 1,000 plated cells for CFU assays. At each time point, viable cell numbers and purity or clonogenicity of target populations were used to calculate the endpoint of fold expansion or cumulative fold expansion over pre-culture numbers. Target population purity and clonogenicity were also used as end-points. Real time PCR of gene expression was quantified relative to the average of two house-keeping genes, and determined relative to expression found with TSFI in 10% oxygen.

To determine the effect of culture conditions on HSC, cord blood units were enriched for CD34+ cells, with a minimum of ≥80% CD34+ purity and viability for expansion studies. Changes in cultured hematopoietic cell populations were assessed in three ways: 1) phenotypically, by flow cytometry of surface markers; 2) functionally, with CFU assays; and 3) genomically, by real-time PCR (FIG. 4). Purity or clonogenicity of target populations post-culture, fold expansion in target population numbers, and relative gene expression were used as end-points (FIG. 5).

Ex Vivo Expansion

Cryopreserved cells were thawed at 37° C., transferred drop-wise to 10× volume of Stemline II media (Sigma Aldrich), centrifuged at 400 rcf for 10 minutes at room temperature, and resuspended in Dulbecco's Phosphate-Buffered Saline (D-PBS, Invitrogen) for manual viability cell counts with Trypan Blue stain (Sigma Aldrich).

CD34+ enriched cells were cultured in tissue culture wells (Interpath) coated with 10 µg/ml RetroNectin (recombinant human fibronectin fragment, Scientifix), and seeded at 0.5× $10^4$ viable cells per 1.1 $cm^2$ in 1 ml Stemline II media. Media was supplemented with human recombinant growth factors (Millipore): Thrombopoietin (T, 50 ng/ml)±Stem Cell Factor (S, 50 ng/ml)±Flt-3 Ligand (F, 80 ng/ml)±Interleukin-6 (I, 100 ng/ml) (T, TS, TSF, TSFI), compared to Thrombopoietin+Stem Cell Factor+Granulocyte Colony-Stimulating Factor (TSG) (each 100 ng/ml, Stemline II manufacturer's recommendations). Cells were cultured in physiologically-relevant oxygen levels consistent with peripheral blood (10%, ~75 mmHg), cord blood (5%, ~38 mmHg), and bone marrow (2.5%, ~19 mmHg) (Galaxy R+ incubators, HD Scientific) and compared to ambient oxygen levels (20%, ~150 mmHg) (Heraeus incubator, KI Scientific), giving a total of 20 separate conditions.

For single-step expansion cells were cultured for 8 days before harvesting, and for serial expansion cells were reseeded at 2×$10^4$ then 3×$10^4$ viable cells per 1.1 $cm^2$ after 1 and 2 weeks of culture, respectively. Cells were harvested by pipetting and D-PBS washes, followed by viability counts with Trypan Blue stain.

Enriched CD34+ cells were cultured with the step-wise addition of growth factors T, TS, TSF, TSFI, and compared to TSG—recommended by manufacturers of FDA-approved HSC expansion media, Stemline II—and for all combinations, cells were cultured in physiologically-relevant oxygen levels of 2.5%, 5% and 10%, and ambient (20%).

Target population purity was determined phenotypically by flow cytometry. Within this study, the average pre-culture value for 7AAD viability was 85±5%, and purity for CD45+ CD34+, CD133+, and CD34+CD38−− were 81±5%, 61±8% and 2.8±0.1%, respectively (data not shown). For post-culture populations, viability across oxygen groups was considerably lower with thrombopoietin alone (T, 60±6%) compared to all other growth factor combinations (>81±3%, p≤0.01) (FIG. 1). The purity of CD45+CD34+ was 24±2%, and of CD34+CD38−− cells 2.2±0.4%. However, insufficient cells from the T alone condition were available for further analysis. Addition of stem cell factor (S) resulted in no change in CD45+CD34+ purity, but increased the percentage of CD34+CD38−− (4.8±0.6%, p≤0.01) to higher than pre-culture levels. No significant difference in purity was observed by the addition of Flt-3 ligand (F). Addition of Interleukin-6 (I) had no effect on CD133+ purity (12±1%), but resulted in a loss of purity of CD45+CD34+ and CD34+CD38−− cells compared to TS or TSF. Purity of all target populations was lowest with TSG (p≤0.01). Interestingly, an oxygen effect was observed, with 20% oxygen resulting in the greatest purity across all target populations (p≤0.01) (FIG. 1).

Examination of fold expansion showed increased numbers of viable cells in 5% and 10% oxygen, and the lowest expansion when cultured in ambient (20%) oxygen. Fold expansion of CFU-GM was also enhanced in 5% oxygen, and expansion of total blast/colony-forming units was enhanced in 5% and 10% oxygen. Additionally, the intermediate level of fold expansion observed in 2.5% oxygen in this study is consistent with both in vivo and in vitro data.

Phenotypic Analysis by Flow Cytometry

Target cell purity was determined pre- and post-culture by flow cytometry (FACSCalibur, Becton Dickinson) with: CD45-FITC+CD34-PE+7AAD, CD34-FITC+CD133-PE+ 7AAD and CD38-FITC+CD34-PE+7AAD for HSC, HPC and multipotent cells (CD133-PE Miltenyi Biotec); and CD61-FITC+CD34-PE+7AAD, CD11b-FITC+CD14-PE+ 7AAD, CD3-FITC+CD19+7AAD (CD11b-FITC Beckman Coulter; others BD Biosciences) for lineage committed cells (FIG. 4). Viable CD45$^+$CD34$^+$ populations were determined using the Miltenyi Biotec modified ISHAGE protocol, and CD34$^+$CD38$^-$ gates were determined according to published recommendations. CD34$^+$ enriched samples used for expansion experiments had greater than 80% 7AAD viability and CD34$^+$ purity.

Functional Analysis by Colony-Forming Unit (CFU) Assay

Pre- and post-culture cells were seeded in 'Complete' methylcellulose medium with recombinant cytokines (H4434; STEMCELL Technologies), and incubated for 14 days for enumeration of blast forming unit-erythrocyte (BFU-E), colony-forming unit-granulocyte/macrophage (CFU-GM), colony-forming unit-granulocyte/erythrocyte/ monocyte/macrophage cells (CFU-GEMM), and total blast/ colony-forming units, as per manufacturer's instructions (FIG. 4).

Clonogenicity was determined by number of colony-forming units per 1,000 cells. Pre-culture values for BFU-E and CFU-GM were 71±5 and 74±5, CFU-GEMM 13±2 and total blast/colony-forming units 158±5 per 1,000 cells (data not shown). Post-culture assessment showed TS resulted in the highest number of BFU-E, CFU-GM, CFU-GEMM and total blast/colony-forming units (44±5, 31±3, 4.8±0.5, and 80±6 colonies per 1,000 cells). TSF resulted in lower clonogenicity of BFU-E, CFU-GEMM and total blast/ colony-forming units, which was further reduced with TSFI for BFU-E and total blast/colony-forming units. Culture with TSG resulted in values equivalent to TSFI for BFU-E and total blast/colony-forming units, but an even lower number of CFU-GEMM (p≤0.01) (FIG. 1).

Across all populations, greatest post-culture purity and clonogenicity was obtained with TS±F. Of particular interest is the increase in purity of CD34+CD38−− cells with TS, to higher than pre-culture levels. Both phenotypically and functionally, target populations were the least pure in the presence of TSG. Additionally, an oxygen effect was observed, with target population purity enhanced at ambient levels, but not in clonogenicity.

RNA, cDNA and Real Time-PCR

Pre- and post-culture samples were stored in Trizol (Invitrogen) until RNA isolation using an RNAspin mini RNA Isolation Kit (Illustra), and quantification using the Nano-Drop Spectrophotometer (Thermo Scientific). Reverse transcription was performed with Superscript III First Strand Synthesis kit (Invitrogen) using random hexamers. Real-time PCR was performed using 7500 FAST Real time PCR System (Applied Biosystems). SybrGreen PCR Master Mix (Applied Biosystems) was used for primer pairs corresponding to HoxB4 (Forward: 5'-CCTGGATGCGCAAAGTTCA-3'—SEQ ID: 7, Reverse: 5'-GCTTGGGCTCCCCGC-3'— SEQ ID: 8) and Nf-yα (Forward: 5'-GATGGTCATGATGGTTCCTG-3'—SEQ ID: 9, Reverse: 5'-GGTATTGTTTGGCATTCACG-3'—SEQ ID: 10) (Sigma Genosys). Taqman PCR Master Mix (Applied Biosystems) was used for CD34 pre-optimised Gene Expression Assay (Hs00156373_m1; Applied Biosystems), and for house-keeping genes Beta Actin (Forward: 5'-GACAGGATGCAGAAGGAGATTACT-3'—SEQ ID: 11, Reverse: 5'-TGATCCACATCTGCTGGAAGG-3'— SEQ ID: 12, Probe: fam-ATCATTGCTCCTCCTGAGCG-CAAGTACTC-tamra—SEQ ID: 13) and GAPDH (Forward: 5'-CCACATCGCTCAGACACCAT-3'—SEQ ID: 14, Reverse: 5'-CCAGGCGCCCAATACG-3'—SEQ ID: 15, Probe: fam-AAGGTGAAGGTCGGAGTCAACG-GATTTG-tamra—SEQ ID: 16) (Sigma Genosys).

At each time point, gene expression levels were quantified relative to the average of both house-keeping genes (FIG. 5). Gene expression during serial expansion was determined relative to TSFI in 10% oxygen. Results are presented as the mean±standard error. One-way ANOVA with Tukey's comparison was performed utilising software program Minitab (version 15), with a significance level of p≤0.05.

Purity and Fold Expansion Determination

Cells assessments were performed pre- and post-culture for single-step expansion, and weekly during serial expansion. Pre- and post-culture target population purity and colony-forming unit clonogenicity were used to determine the overall change in cell population proportions (FIG. 5).

Fold expansion reflected the increase in target cell numbers following culture. At each time point, the viable cell number is multiplied by the purity or clonogenicity of specific target populations, thereby giving the target cell number at each time point. These numbers are compared pre- and post-culture to determine the fold expansion of these target cell populations. Cumulative fold expansion indicates the fold expansion of target population numbers over successive weeks.

Results are presented as the mean±standard error. Two-way ANOVA using General linear model statistical analysis was performed with Tukey's pairwise comparison, with a significance level of p≤0.05.

Clinically Valid Enhanced Fold Expansion of HSC, HPC and Multipotent Cells

Figure 2:
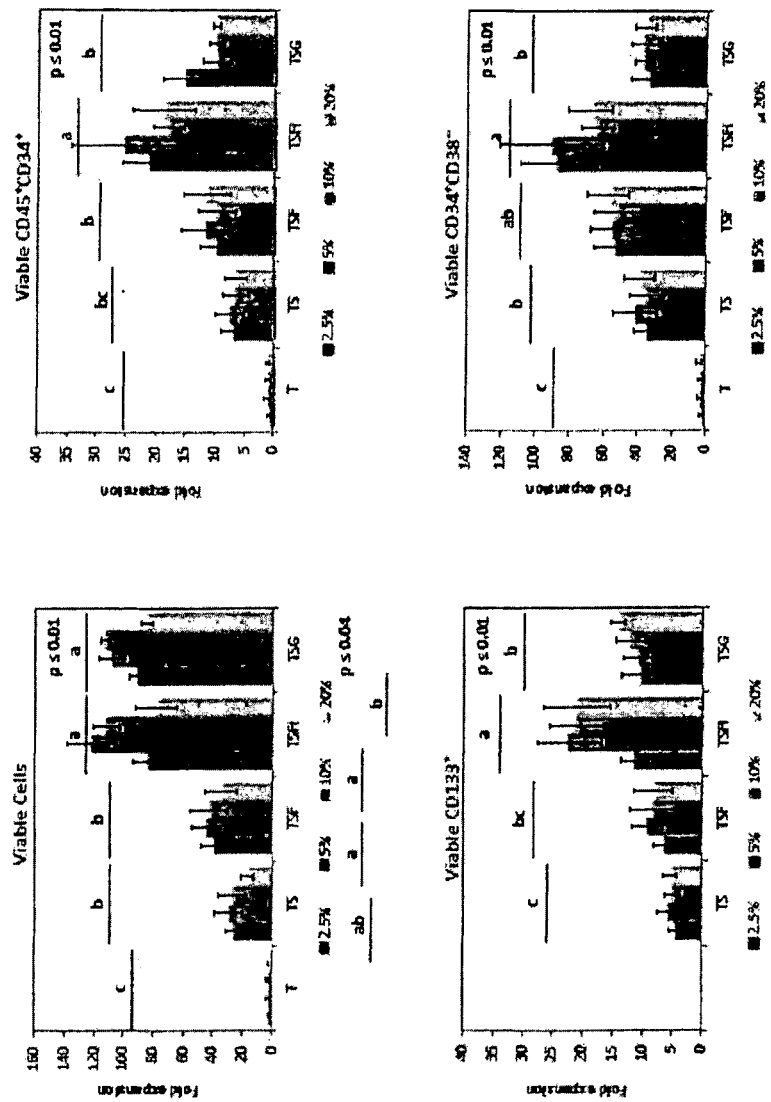
FIG. 2 shows the fold expansion of HSC, HPC and multipotent cells, assessed phenotypically and functionally. The effect of growth factor combination and oxygen level on the fold expansion of target populations was determined by manual counts, flow cytometry and colony-forming unit counts. Fold expansion illustrates the increase in target population numbers over pre-culture values. Growth factor combinations were thrombopoietin (T, 50 ng/ml), stem cell factor (S, 50 ng/ml), Flt-3 ligand (F, 80 ng/ml) and Interleukin-6 (I, 100 ng/ml) (T, TS, TSF, TSFI), compared to thrombopoietin, stem cell factor, and granulocyte colony-stimulating factor (TSG, each 100 ng/ml). Oxygen levels tested were 2.5%, 5%, 10% and 20%. N=4 independent cord blood units, each performed in triplicate. Results are expressed as mean±standard error of the mean. Letters a-c indicate statistically different groups, with p values as shown.
Figure 2:
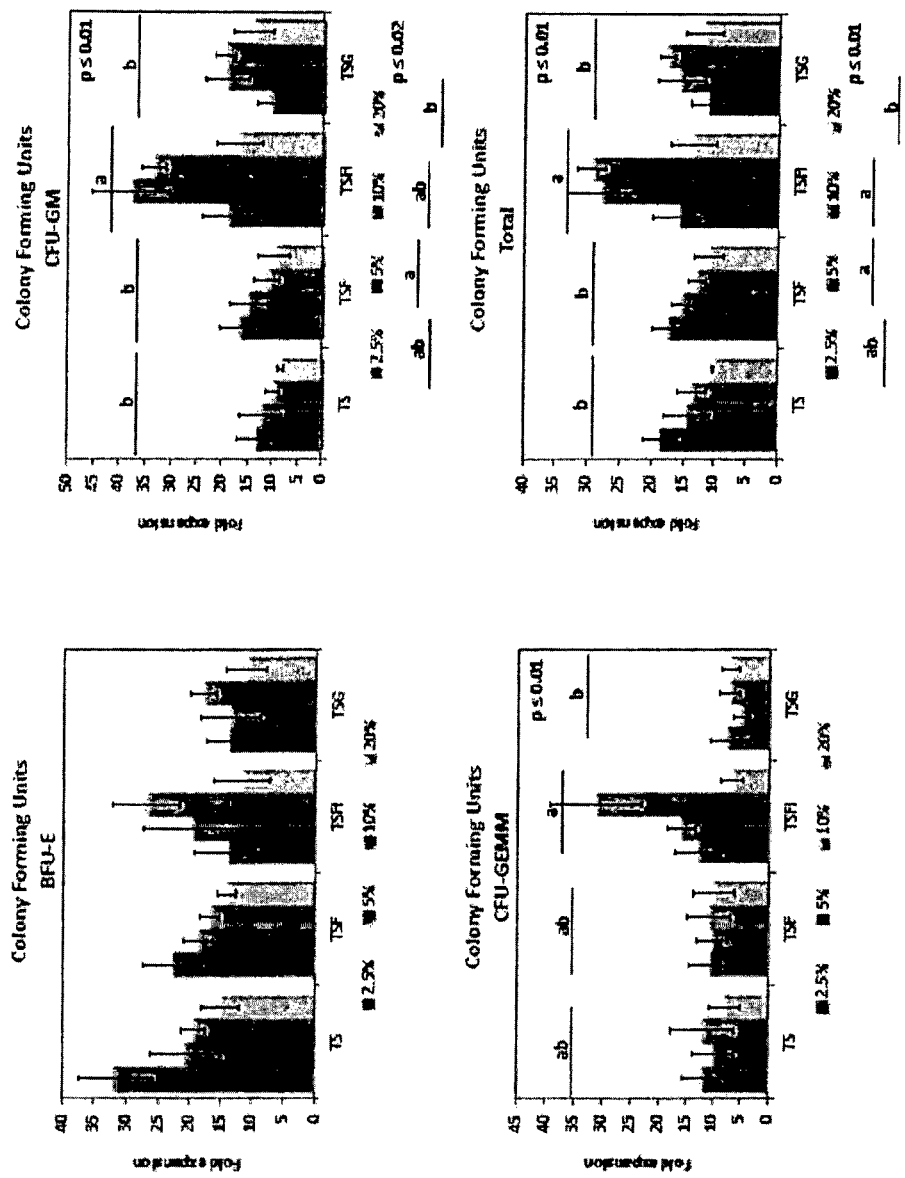

Of primary clinical interest is the fold expansion of cell populations, which represent the increase in transplantable cell dose. Thrombopoietin (T) alone was insufficient to ensure clinically valid expansion, with only a doubling of viable cell numbers (2.0±0.3), no change in CD45+CD34+ cell numbers, and only a doubling in CD34+CD38−− cell numbers (2.6±0.8) (FIG. 2). There were insufficient cells for analysis of CD133+ cells, or CFU assays. Addition of stem cell factor (S) increased expansion of viable cells to 25±4 fold, with a corresponding increase in all target populations. Minimal enhancement was observed with the addition of Flt-3 ligand (F). However, inclusion of interleukin-6 (I) in the culture media greatly enhanced fold expansion of viable cells (99±7 fold) and all target populations ($p \leq 0.01$) (FIG. 2). Specifically, CD45+CD34+, CD133+, and CD34+CD38−− cell numbers were expanded 21±3, 19±2, and 78±10 fold, respectively. TSG resulted in similar fold expansion of viable cells, but not target HSC and HPC populations; indicative of a greater degree of differentiation, primarily down the granulocytic lineage (data not shown). A modest oxygen effect was observed for the viable cell fold expansion, with overall enhancement in 5% and 10% oxygen, and lowest in 20% oxygen ($p \leq 0.04$).

Fold expansion of multipotent cells was determined functionally using CFU assays. There was no effect of growth factor combination or oxygen level on fold expansion of BFU-E (18±1.2 fold) (FIG. 2). However, TSFI greatly enhanced expansion of CFU-GM and total blast/colony-forming units (27±3 and 22±3 fold) compared to all growth factor combinations, and enhanced expansion of CFU-GEMM (17±3) compared to TSG (7±1, $p \leq 0.01$). In addition, 5% oxygen enhanced fold expansion of CFU-GM ($\leq 0.02$), and culture in 5% and 10% oxygen enhanced expansion of total blast/colony-forming units, while 20% oxygen resulted in lower fold expansion for both of these colony types ($p \leq 0.01$). In contrast to purity data, the results from both phenotypic and functional analysis of fold expansion indicate that TSFI results in optimal expansion of HSC, HPC and multipotent cells, with the optimal oxygen levels being 5% and 10%.

Consistent Enhanced Expansion Validated Across Multiple Cord Blood Units

To determine the clinical validity of optimised conditions, fold expansion was assessed in 10 independent cord blood units, each cultured with TSFI in both 5% and 10% oxygen. Mean values for all populations were consistent with data presented in FIGS. 1 and 2, with 87±13 fold expansion of viable cells, 19±3, 17±5 and 73±15 fold expansion of CD45+CD34+, CD133+, and CD34+CD38−− cells, respectively. Mean expansion of clonogenic populations (BFU-E, CFU-GM, CFU-GEMM, total blast/colony-forming units) were between 25±5 to 36±6 (TABLE 1). Although a range of values were seen across target populations, optimised conditions of TSFI in 5% and 10% oxygen resulted in expansion of all populations in all samples, thereby demonstrating robust effects across multiple cord blood units (TABLE 1).

expansion of target cell populations was assessed both phenotypically and functionally. Growth factor combination consisted of thrombopoietin (50 ng/ml), stem cell factor (50 ng/ml), Flt-3 ligand (80 ng/ml), and Interleukin-6 (100 ng/ml). N=10 independent cord blood units, each performed in triplicate.

Serial Expansion with Enhanced Cumulative HSC and Progenitor Fold Expansion

Expansion conditions can result in exhaustion of HSC and a concomitant loss of long-term repopulation potential. Serial expansion indirectly assesses this loss through examination of cumulative fold expansion. The optimised conditions TSFI in 5% and 10% oxygen were compared to TSG in 20% oxygen.

Figure 3:
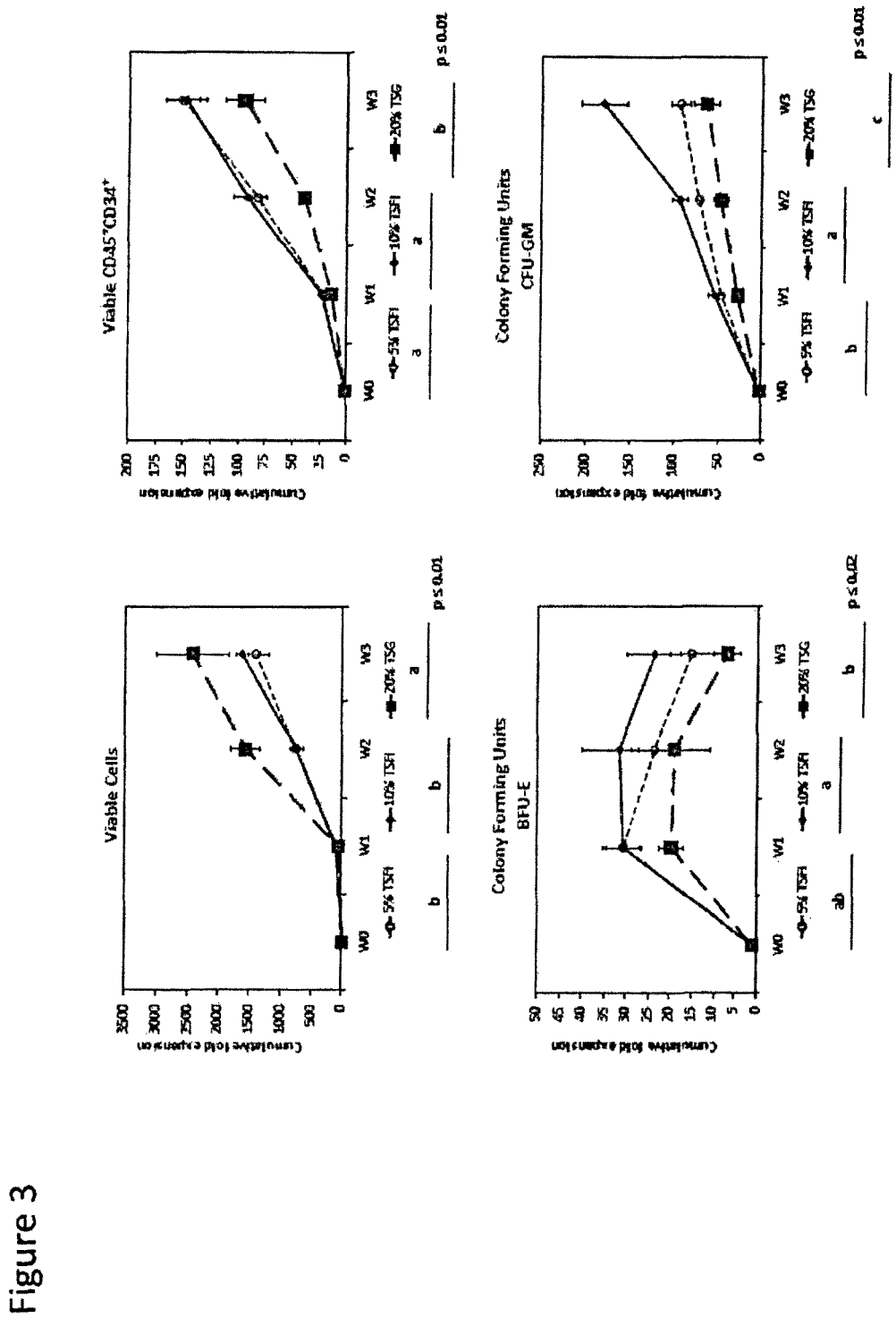
FIG. 3 shows the cumulative fold expansion of target populations, and relative gene expression levels during serial expansion. Cumulative fold expansion of hematopoietic stem, progenitor and multipotent target cells was determined with growth factor combination TSFI in 5% and 10% oxygen compared to TSG in 20% oxygen. Changes in target population cell numbers were assessed on the basis of manual cell counts, detection of cell surface markers, and colony-forming unit counts. Gene expression levels quantified relative to house-keeping genes were determined relative to expression in one condition (TSFI in 10% oxygen) at each time point. N=4 independent cord blood units, each performed in triplicate. Results are expressed as mean±standard error of the mean. Serial expansion was shown across 3 weeks (W0-W3). Letters a-c indicate statistically different groups, with p values as shown.
Figure 3:
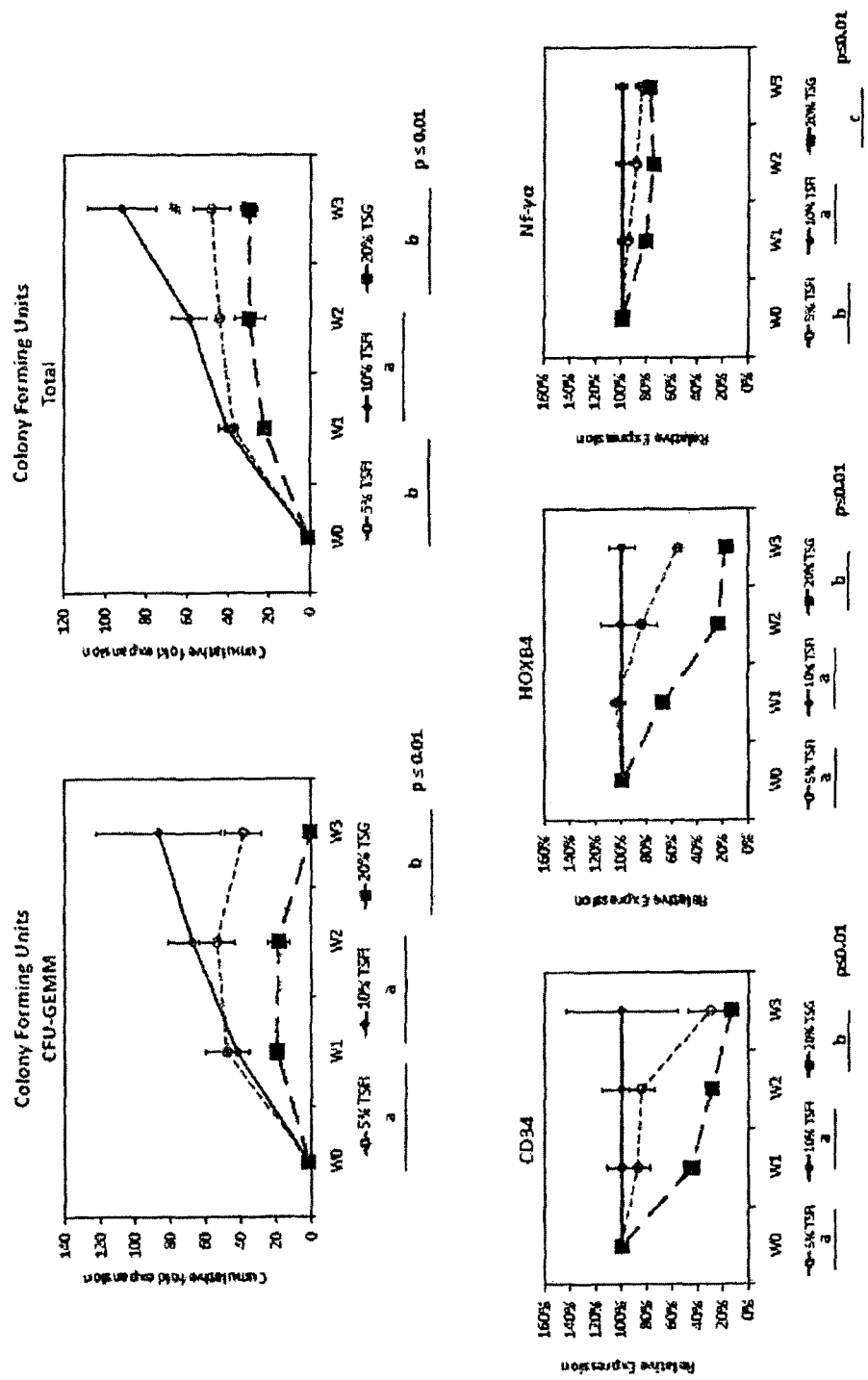

Flow cytometric analysis showed TSG in 20% oxygen resulted in the greatest total viable cell numbers after three weeks in culture; however, this occurred concurrently with lower expansion of CD45+CD34+ ($p \leq 0.01$) (FIG. 3). In comparison, TSFI in 5% and 10% oxygen resulted in enhanced cumulative fold expansion of CD45+CD34+ cells ($p \leq 0.01$). In regards to the expansion of neutrophilic and megakaryocytic precursors, TSG in 20% oxygen resulted in predominantly granulocytic differentiation, while TSFI in 5% and 10% oxygen resulted in enhanced expansion of megakaryocytic cells (CD61+), and continued expansion of granulocytic cells (CD11b+ CD14−, N=1 cord blood in triplicate, data not shown). At no point in single-step or serial expansion were B cells (CD19+) or T cells (CD3+) detected, thereby confirming low immunogenicity of expanded cells was maintained (data not shown, N=4 cord blood, each in triplicate).

Functional assessment over 3 weeks of serial expansion showed TSG in 20% oxygen resulted in low cumulative fold expansion of BFU-E which dropped below initial expansion levels in week 3, with simultaneous complete exhaustion of CFU-GEMM. In comparison, cumulative fold expansion was enhanced with TSFI in 5% oxygen (CFU-GM and CFU-GEMM) and with TSFI in 10% oxygen (all blast and colony-forming units, $p \leq 0.02$). Notably, TSFI in 10% oxygen showed significantly enhanced expansion of CFU-GM and total blast/colony-forming units when compared with both 5% TSFI and 20% TSG ($p \leq 0.01$) (FIG. 3).

In accordance with single-step and serial expansion findings, the relative gene expression levels for hematopoietic stem and progenitor marker CD34, and for HSC self-renewal associated genes HoxB4 and Nf-yα were highest with TSFI in 10% oxygen, and higher with TSFI in 5% and 10% oxygen than TSG 20% oxygen ($p \leq 0.01$), indicative of a greater proportion of CD34+ cells and self-renewing HSC present throughout the culture period (FIG. 3). In summary, analysis of all target populations and relative gene expres-

| | Fold Expansion | | | | | | | |
|---|---|---|---|---|---|---|---|---|
| | Viable cells | Viable CD45+ CD34+ | Viable CD133+ | Viable CD34+ CD38−− | BFU-E | CFU-GM | CFU-GEMM | Total BFU/CFU |
| Mean ± standard error of the mean | 87 ± 13 | 19 ± 3 | 17 ± 5 | 73 ± 15 | 25 ± 5 | 36 ± 6 | 30 ± 6 | 30 ± 5 |
| Median | 87 | 21 | 15 | 73 | 26 | 39 | 30 | 33 |
| Range | 17-148 | 7.1-36 | 3.5-36 | 22-122 | 2.9-47 | 1.8-61 | 1.4-67 | 2.1-54 |

TABLE 1 shows the validation of cord blood ex vivo expansion with TSFI in 5% and 10% oxygen. Clinical validity of optimised conditions (TSFI in 5% and 10% oxygen) was determined for multiple cord blood units. Fold sion levels indicate that TSFI in 10% oxygen results in the greatest cumulative fold expansion and proportion of HSC, HPC and multipotent cells, with a reduced likelihood of HSC and HPC exhaustion.

Example 2

Long-Term Cultures

CD34+ hematopoietic progenitor cells were derived from human umbilical cord blood, isolated using magnetic anti-human CD34+ beads (Miltenyi Biotec). All culture conditions were seeded with $1-2 \times 10^4$ cells in Stemline medium (Millipore) containing growth factors and other additives as in EXAMPLE 1. Cultures were performed in triplicate of each culture condition. Accordingly, each culture condition used three culture wells, each seeded with $1-2 \times 10^4$ CD34$^+$ cells in 1 ml of medium. All experiments were performed independently on at least three different cord blood samples. Cells were cultured in the presence of 2%, 5%, 10% or 20% (atmospheric) oxygen tensions in a low oxygen incubator. Oxygen tensions were monitored regularly through the culture period After 8 days of culture, all cells were harvested from all culture wells, counted, and surface antigen stained. Antibodies used for surface phenotype determination include anti-CD34 (BD Biosciences), anti-CD133 (Miltenyi Biotec), anti-CD38 (BD Biosciences and anti-CD45 (BD Biosciences) antibodies to evaluate progenitor cell distributions. Cell viability was assessed by staining with 7AAD. Flow cytometry analysis of the cells was performed using multi-parameter FACScan flow cytometry analysis and according to the methods described in EXAMPLE 1. Cells were gated according to size (forward and side scatter) and viability (7AAD−). Appropriate controls included matched isotype antibodies to establish positive and negative quadrants, as well as appropriate single colour stains to establish compensation. For each sample, at least 10,000 list mode events were collected.

Colony-Formation Assays

To determine whether HPCs retain the ability to produce myeloid and erythroid colonies, methylcellulose assays were performed as follows. Cells were added at $1 \times 10^4$/ml to 3.0 ml of methylcellulose medium with cytokines (IL-3 20 ng/ml; GMCSF 30 ng/ml; erythropoietin 3 IU/ml; stem cell factor 50 ng/ml; all Stem Cell Technologies, Vancouver) plus 0.5 ml of DMEM (2% FCS, 10 IV/ml penicillin, 10 ug/ml streptomycin, 1 mM L-glutamine). 1 ml of this mixture was added to a scored Petri dish using a syringe and a blunt needle to avoid bubbles. Triplicate assays were performed for each condition. The Petri dishes were then placed in an incubator with 5% $CO_2$ at 37° C. for 10-14 days. After 10-14 days, the number of colonies were determined by manual counting. Positive colonies were scored on the basis of an accumulation of 40 or more cells. Erythroid colonies were scored after 14-21 days on the basis of a gold-brown pigment, demonstrating hemoglobin, whereas myeloid colonies were identified by their predominantly transparent appearance. Mixed colonies were defined as colonies containing myeloid cells, erythroid cells and megakaryocyte precursors.

Example 3

Optimisation of Culture Conditions

Figure 6:
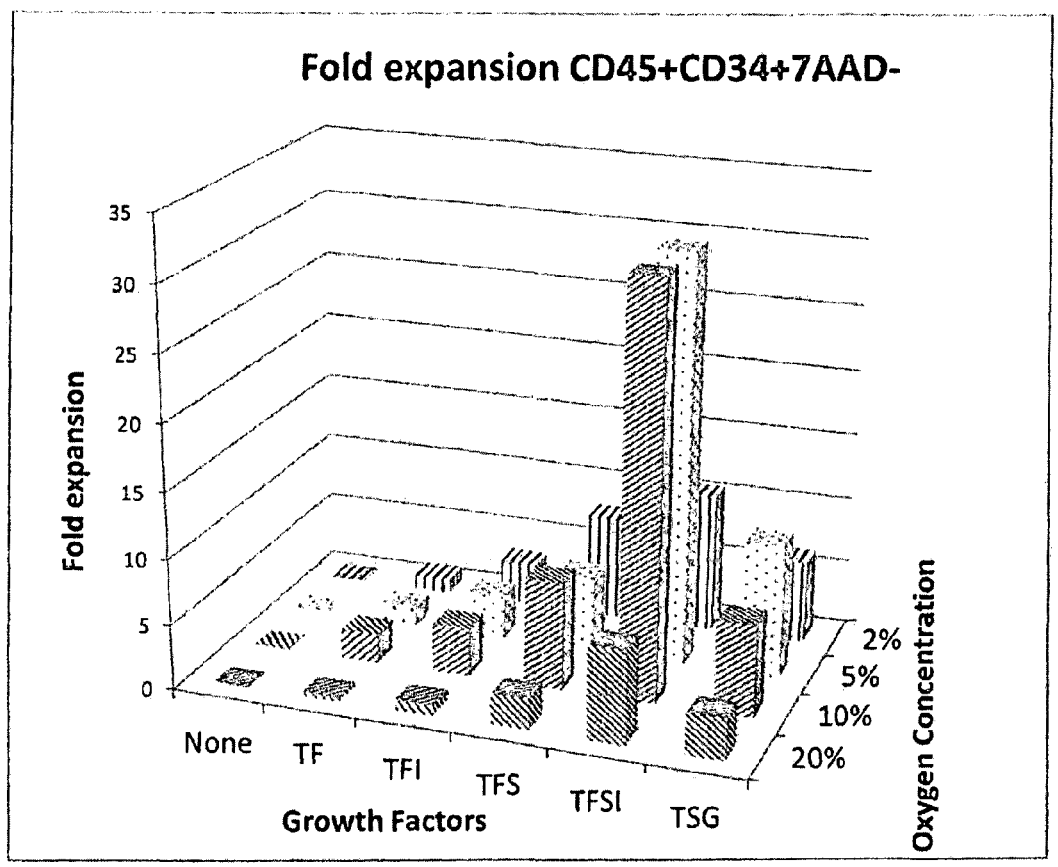
FIG. 6 shows the fold expansion of total cells and of HSC subsets defined by phenotypic markers (CD34+CD45+ 7AAD−) in the presence of different growth factor combinations (at the concentrations indicated in the text) and at different oxygen concentrations (2%, 5%, 10%, and room air (20% $O_2$)). Data are the mean of 10 different experiments, and all values are calculated as the fold expansion compared to the seeded population. (None—No growth factors added; TF—Thrombopoietin, Flt-3 ligand; TFI—Thrombopoietin, Flt-3 ligand, Interleukin-6; TFS—Thrombopoietin, Flt-3 ligand, SCF; TFSI—Thrombopoietin, Flt-3 ligand, SCF, Interleukin-6; TSG—Thrombopoietin, SCF, G-CSF)
Figure 7:
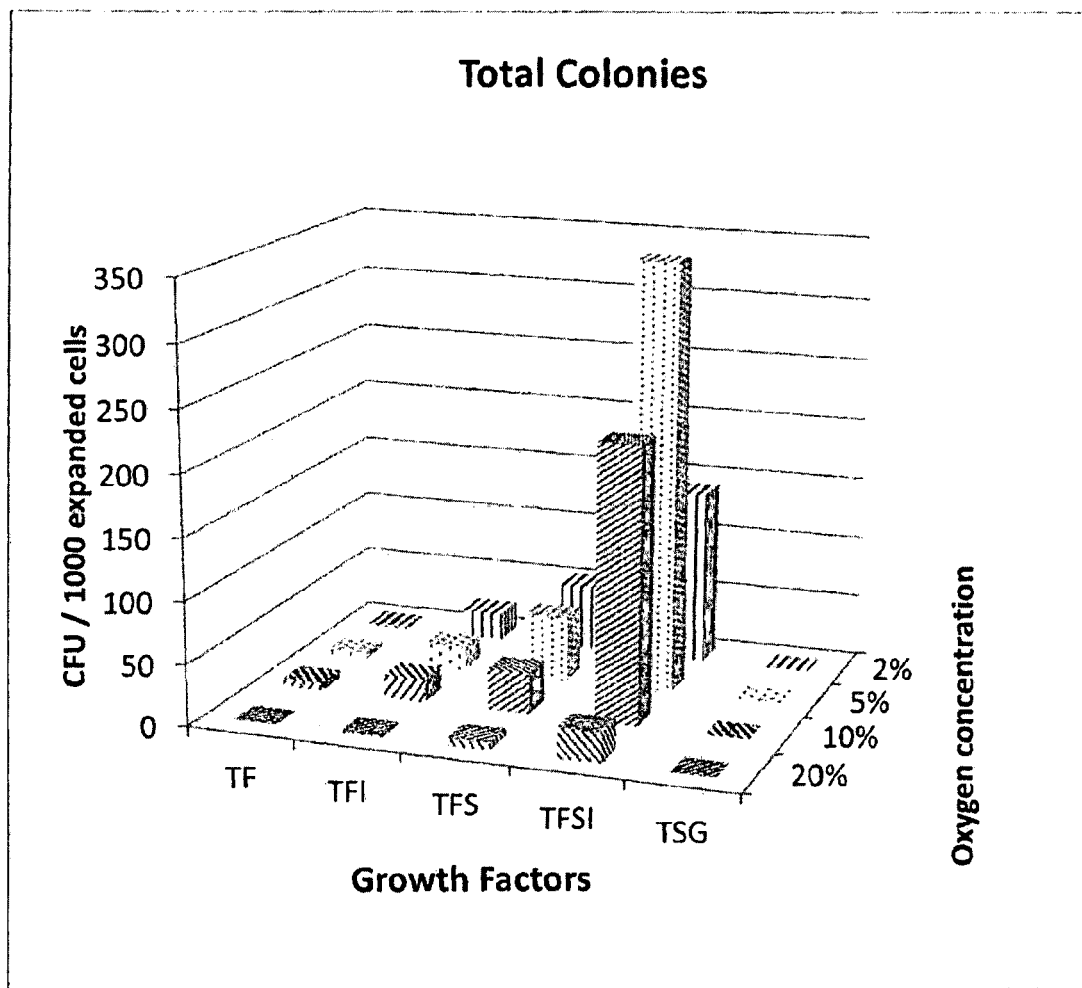
FIG. 7 shows the total colonies per 1000 cells in each of the culture conditions described in FIG. 6.

Cells from 10 different umbilical cord blood samples were cultured for 8 days in the presence of different combinations of growth factors, consisting of Thrombopoietin, 50 ng/ml, Flt-3 ligand 80 ng/ml, Interleukin-6, 100 ng/ml, Stem cell factor (SCF), 50 ng/ml, and G-CSF 100 ng/ml in the presence of 2%, 5%, 10% or 20% oxygen (FIG. 1). In all samples tested, the combination of Thrombopoietin, Flt-3 ligand, SCF and Interleuki-6 (TFSI) in either 5% or 10% $O_2$ gave the greatest total expansion of CD34+CD45+ hematopoietic cells, averaging a 30 fold increase (compared to the pre-culture values) (FIG. 6). This was even more evident in the colony assays (FIG. 7).

It has been demonstrated that the cellular variability between cord blood units can impact on expansion capability. The optimised ex vivo expansion conditions as described above were tested to confirm consistency using ten independent cord blood units. It was found that in those expanded with TSFI in both 5% and 10% oxygen, all target populations in every cord blood sample underwent expansion. As the average banked cord blood unit contains only sufficient cells for transplantation into recipients weighing <40 kg (Kogler G., et al., 1998), fold expansion values of >3 are the preferred minimal target for clinical applicability. The optimised conditions demonstrated that this could be achieved in 9 out of 10 samples, with the remaining cord blood unit showing reasonable expansion by phenotypic assessment (3.5 to 22 fold) and 1.4 to 2.9 fold expansion by functional assays. Consistent achievement of higher expansion values enable protocols in which partial cord blood volumes are expanded, allowing for possible transplantation of both unmanipulated and expanded cells from the same cord blood unit, thereby maximising the likelihood of long-term engraftment with minimal reconstitutional delay and no increase in GvHD.

The long-term repopulation potential utilising the optimised culture conditions were assessed and it was determined that the optimised conditions of TSFI in 5% and 10% oxygen resulted in significantly higher cumulative fold expansion in all target cell and colony populations, compared to TSG (Thrombopoietin (T)+Stem Cell Factor (S)+ Granulocyte Colony-Stimulating Factor (G)) in 20% oxygen. Moreover, TSFI in 10% oxygen showed enhanced and continual expansion of CD45$^+$CD34$^+$ cells, CFU-GM, CFU-GEMM and total blast/colony-forming units, thereby demonstrating greater maintenance and expansion of hematopoietic stem and progenitor cells over time. In comparison, TSG in 20% oxygen resulted in differentiation, and exhaustion of CFU-GEMM, indicating a loss of self-renewing HSC. It was found in using the optimised culture conditions as described above that the relative expression levels of clinically relevant gene CD34$^+$ and self-renewal associated genes HoxB4 and Nf-yα (Sharma, S., et al., 2006; Zhu J., et al., 2005; Stein M. I., et al., 2004) were highest with TSFI in 10% oxygen, and higher in 5% and 10% TSFI compared to TSG in 20% throughout serial expansion.

Example 4

Effect of Ficolins

Figure 8:
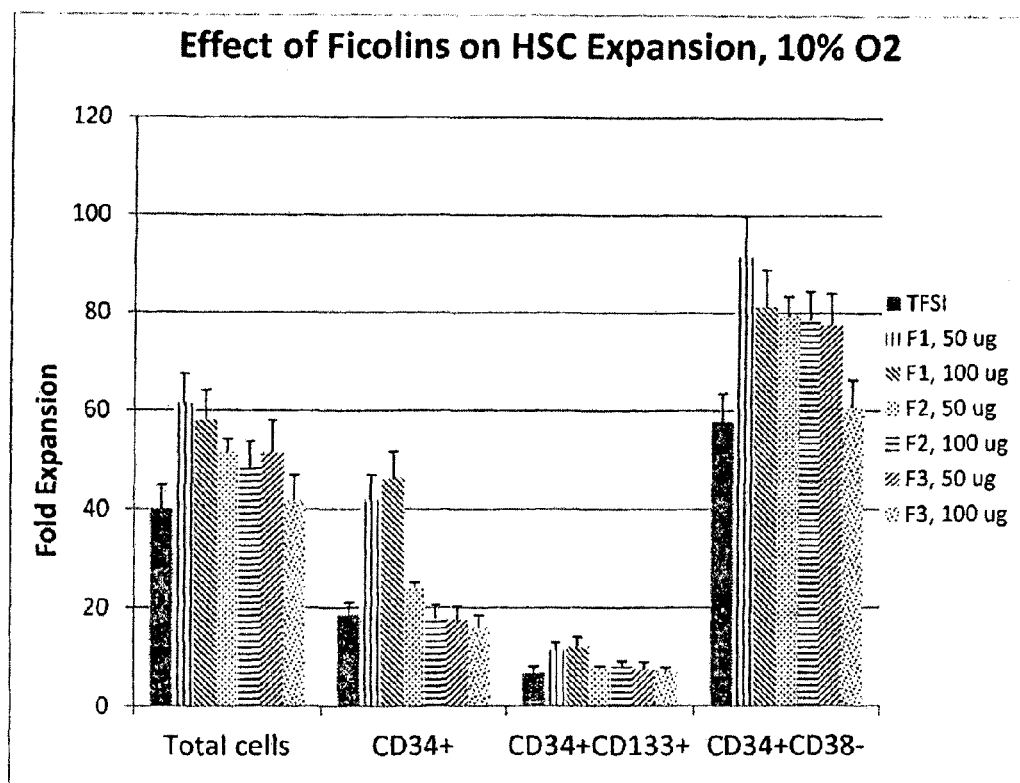
FIG. 8 shows the fold expansion of total cells and of HSC subsets defined by phenotypic markers—CD34+, CD34+ CD133+ and CD34+CD38−. All analyses were gated for viable cells only (7AAD−). Cells were culture in the presence of TFSI growth factors, with or without the addition of ficolins-1, ficolin-2, or ficolin-3 at 50 ng/ml or 100 ng/ml, in 10% oxygen.
Figure 9:
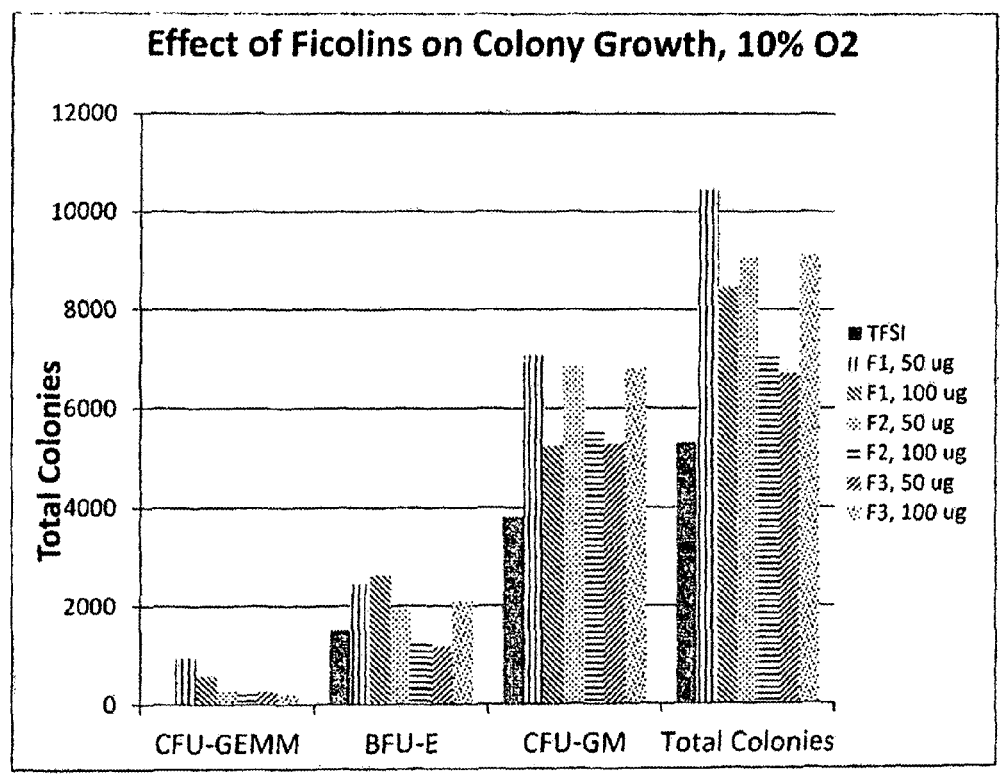
FIG. 9 shows the total colony numbers and colony morphology of cells cultured in the presence of TFSI+/− ficolins-1, ficolin-2, or ficolin-3 at 50 or 100 ng/ml in 10% $O_2$. After 8 days of culture in these growth factors, 1000 cells from each condition were seeded into semisolid media (Methocult, Stem Cell Technologies, Vancouver) in triplicate for each condition and cultured for a further 12-14 days. Colony numbers and types were then counted under an inverted microscope.

Taking the best method from Example 3 (TFSI in 5% or 10% $O_2$), the effect of adding ficolins-1, ficolin-2, or ficolin-3 to the culture media at either 50 ng/ml, 100 ng/ml or 200 ng/ml in the presence of TFSI growth factors was examined. For all ficolins, the addition of 200 ng/ml did not prove significantly beneficial in any of the experiments (data not shown). Ficolin-1 induced a consistent increase in total cell numbers, as well as CD34+ cells, CD34+CD133+ and CD34+CD38− cells, at both 50 ng/ml and 100 ng/ml, most notably at 10% $O_2$. (FIG. 8). This enhanced expansion was also reflected in increased colony forming units (FIG. 9). Despite the less marked effects of ficolin-1 on phenotypic expansion at 5% $O_2$ (FIG. 10), this culture condition was most effective at expanding colony forming units, with a greater than 3-fold increase in total colonies seen at 100 ng/ml in 5% $O_2$, compared to TFSI alone (FIG. 11).

Figure 10:
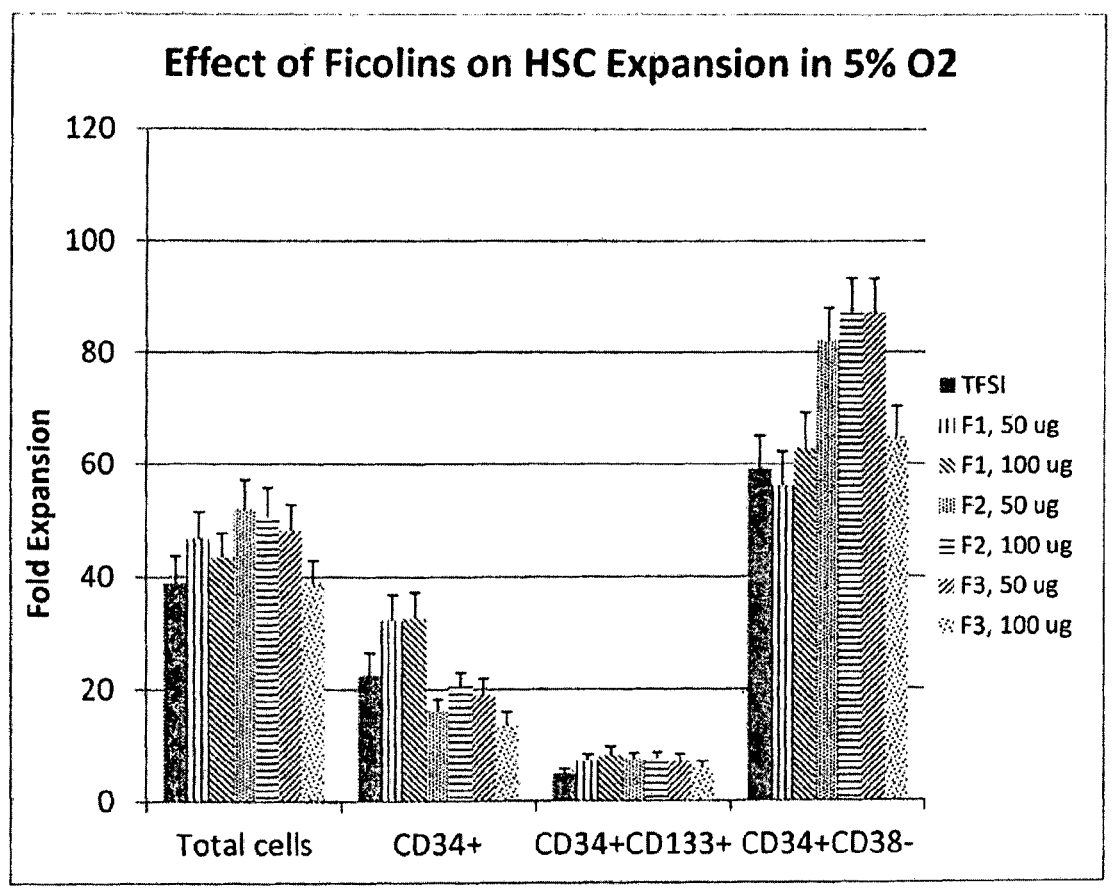
FIG. 10 shows the fold expansion of total cells and of HSC subsets defined by phenotypic markers—CD34+, CD34+CD133+ and CD34+CD38−. All analyses were gated for viable cells only (7AAD−). Cells were culture in the presence of TFSI growth factors, with or without the addition of ficolins-1, ficolin-2, or ficolin-3 at 50 ng/ml or 100 ng/ml, in 5% oxygen.
Figure 11:
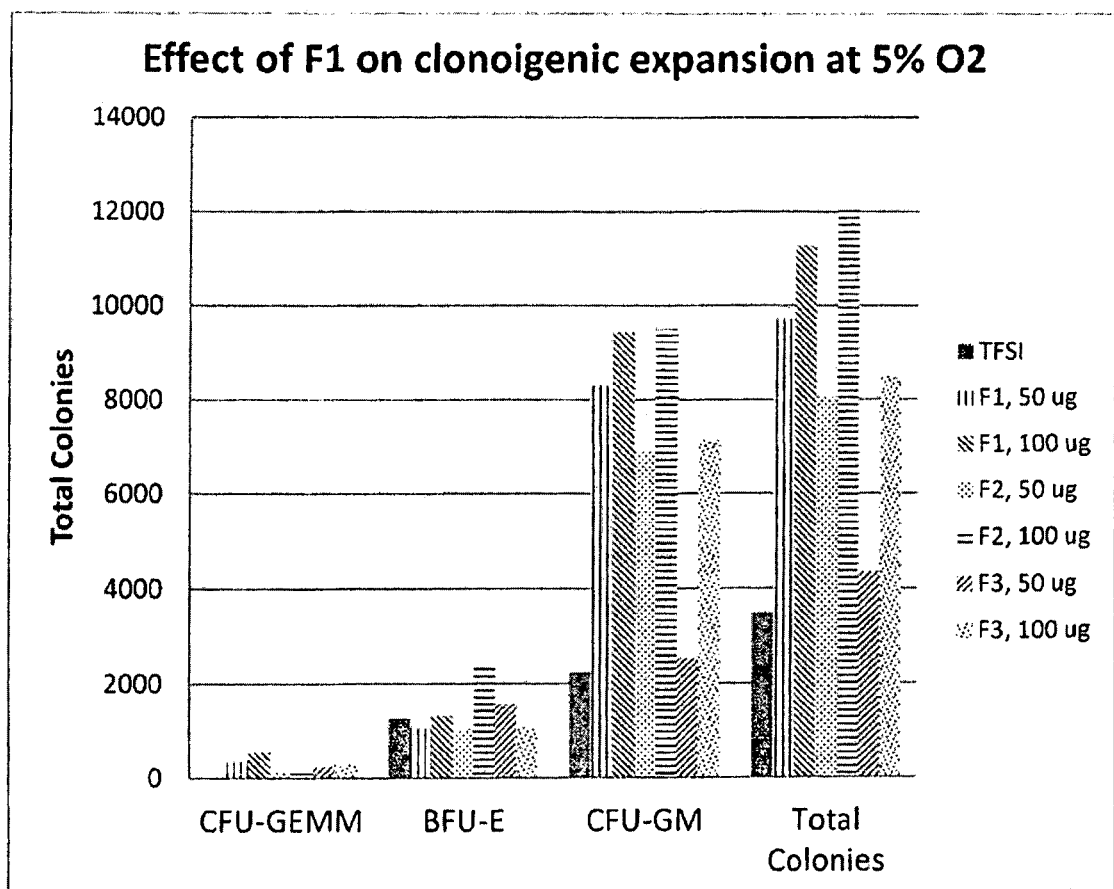
FIG. 11 shows the total colony numbers and colony morphology of cells cultured in the presence of TFSI+/− ficolins-1, ficolin-2, or ficolin-3 at 50 or 100 ng/ml in 5% $O_2$. After 8 days of culture in these growth factors, 1000 cells from each condition were seeded into semisolid media (Methocult, Stem Cell Technologies, Vancouver) in triplicate for each condition and cultured for a further 12-14 days. Colony numbers and types were then counted under an inverted microscope.

The effects of ficolin-2 on phenotype were minimal at 10% $O_2$ (FIG. 6), but more marked at 5% $O_2$ (FIG. 10). Again, the expansion measured by phenotype underestimated the degree of expansion of colony forming cells at both oxygen concentrations (FIG. 9, FIG. 11). This discrepancy is even more marked with ficolin-3, where there was no evidence of expansion of phenotypically defined HSC's at either oxygen concentration (FIG. 8, FIG. 10), but clear expansion of colony forming cells, particularly at 100 ng/ml (FIG. 9, FIG. 11).

Of particular note in all experiments is the maintenance of the most primitive class of colony forming cells, CFU-GEMM, in the presence, but not in the absence, of ficolins (FIG. 9, FIG. 11), indicating that these agents selectively preserve primitive HSC populations.

It is to be understood that various other modifications and/or alterations may be made without departing from the spirit of the present invention as outlined herein.

We claim:

1. A method of extending ex vivo viability of a HPC and/or HSC population, or culturing or expanding a HPC and/or HSC population said method comprising culturing the HPC and/or HSC population in the presence of at least one of ficolin-1, ficolin-2, or ficolin-3.

2. The method according to claim 1, wherein renewal capacity and/or pluripotency of the HPC and/or HSC is maintained or increased.

3. The method according to claim 1, wherein the HSC and/or HPC are further cultured in an environment wherein a concentration of oxygen is less than a normal ambient oxygen concentration.

4. The method according to claim 1 wherein the HSC and/or HPC are cultured in the presence of at least one of ficolin-1, ficolin-2, or ficolin-3 at a concentration of in the range of approximately 50 ng/ml-200 ng/ml.

5. The method according to claim 1 wherein the HSC and/or HPC are cultured in the presence of ficolin-1.

6. The method according to claim 3 wherein the concentration of oxygen is less than approximately 20%, or is less then approximately 12%, or is between approximately of 5%-10% or is approximately 5%.

7. The method according to claim 1 wherein the HSC and/or HPC are cultured in the presence of growth factors selected from the group comprising interleukins 3, 6 and 11, stem cell factor, stem cell ligand, FLT-3 ligand, and thrombopoietin.

8. The method according to claim 7 wherein the growth factors are provided at a concentration of about 50 ng/mL-100 ng/mL.

9. The method according to claim 7 wherein thrombopoietin is provided at about 50 ng/mL, stem cell factor is provided at about 50 ng/mL, Flt-3 ligand is provided at about 80 ng/mL and interleukin 6 is provided at about 100 ng/mL.

10. The method according to claim 1 wherein the HPC are cultured to increase the number of HPC relative to the initial number of HPCs to produce a second amount of HPCs.

11. The method according to claim 10, wherein the second amount of HPC are isolated and further cultured in a separate culture medium.

12. The method according to claim 11, wherein the second amount of HPC are isolated and further cultured in a separate culture medium and the separate culture medium comprises a growth factor selected from the group comprising interleukins 3, 6 and 11, stem cell factor, stem cell ligand, FLT-3 ligand, and thrombopoietin that promotes HPC maintenance, expansion and/or differentiation, to produce differentiated cells of hematopoietic origin.

13. The method according to claim 12, wherein the separate culture medium includes inoculated stromal cells and/or is a stromal cell conditioned medium.

14. The method according to claim 1 wherein the HPC are cultured for a period of 6-8 weeks prior to expansion and/or differentiation of HPC and/or HSC.

\* \* \* \* \*

UNITED STATES PATENT AND TRADEMARK OFFICE
CERTIFICATE OF CORRECTION

PATENT NO. : 9,518,250 B2  
APPLICATION NO. : 14/346160  
DATED : December 13, 2016  
INVENTOR(S) : Melinda L. Tursky et al.

It is certified that error appears in the above-identified patent and that said Letters Patent is hereby corrected as shown below:

On the Title Page

Please delete the line at item (73) Assignee: and replace with the following:
"Nohla Therapeutics Australia Pty Ltd, Melbourne, Victoria (AU)"

Signed and Sealed this
Thirtieth Day of May, 2017

Michelle K. Lee
*Director of the United States Patent and Trademark Office*

SEQUENCE LISTING

<160> NUMBER OF SEQ ID NOS: 16

<210> SEQ ID NO 1
<211> LENGTH: 1736
<212> TYPE: DNA
<213> ORGANISM: Homo sapiens

<400> SEQUENCE: 1

```
gctgggtcaa tagtacttgc cgcagtactc ttaaaactag cgatggaggc ttcgacatgg      60
gctttaggga gtcataagtg gagtccggaa agaggtatct gtactataaa agctattgtg     120
taagctagtc atattaagtt gttggctcag gagtttgaag tccttgagag aggattatga     180
tgcgacgtga gtgcgttcgt aatttgagtc tgcttggcag atagtaatga ggatgtaagc     240
ccgtgggcga ttatgagaat gactgcgccg gtgaagcttc aggggggtttg gatgagaatg     300 gctgttacta cgagggctat gtggctgatt gaagagtatg caatgagcga tttttaggtct    360 gtttgtcgta ggcagatgga gcttgttata attatgcctc atagggatag tacaaggaag     420
gggtaggcta tgtgtttgt cagggagttg agaaactgtg gcacaaggcg agagctggtt      480
tcctctgccc tgttagagct gggggactct tcagagtcaa aggccagaga gcatggagct     540
gagtggagcc accatggccc gggggctcgc tgtcctgcta gtcttgttcc tgcatatcaa     600
gaacctgcct gcccaggctg cggacacatg tccagaggtg aaggtggtgg gcctggaggg     660
ctctgacaag ctcaccattc tccgaggctg cccggggctg cccggggccc cagggccaaa      720
gggagaggca ggtgtcattg gagagagagg agaacgcggt ctccctggag cccctggaaa     780
ggcaggacca gtggggccca agggagaccg aggagagaag gggatgcgtg gagagaaagg     840
agacgctggg cagtctcagt cgtgtgcgac aggcccacgc aactgcaagg acctgctaga     900 ccggggggtat ttcctgagcg gctggcacaa tatctacctg cccgactgcc ggcccctgac    960
tgtgctctgt gacatggaca cggacggagg gggctggacc gttttccagc ggaggatgga   1020
tggctctgtg gacttctatc gggactgggc cgcatacaag cagggcttcg gcagtcagct    1080
gggggagttc tggctgggga acgacaacat ccacgccctg actgcccagg gaagcagcga    1140
gctccgtgta gacctggtgg actttgaggg caaccaccag tttgctaagt acaaatcatt    1200
caaggtggct gacgaggcag agaagtacaa gctggtactg ggagcctttg tcggggggcag   1260 tgcgggtaat tctctaacgg gccacaacaa caacttcttc tccaccaaag accaagacaa    1320
tgatgtgagt tcttcgaatt gtgctgagaa gttccaggga gcctggtggt acgccgactg   1380
tcatgcttcg agcctcaatg gtctctacct catgggaccc catgagagct atgccaatgg    1440
tatcaactgg agtgcgcga aggggtacaa atatagctac aaggtgtcag agatgaaggt    1500
gcggcccgcc tagacgggcc aggacccctc cacatgcacc tgctagtggg gaggccacac   1560
ccacaagcgc tgcgtcgtgg aagtcacccc atttccccag ccagacacac tcccatgacg    1620
cccacagctg ccccttttgcc cccagctcag tcaagccgtc acatgcccac aacctcacca  1680
```
gagggagaat tatgtttcta aatatgttta cttttgggga cagaaaaaaa aaaaaa    1736

<210> SEQ ID NO 2
<211> LENGTH: 326
<212> TYPE: PRT
<213> ORGANISM: Homo sapiens

<400> SEQUENCE: 2

Met Glu Leu Ser Gly Ala Thr Met Ala Arg Gly Leu Ala Val Leu Leu
1               5                   10                  15

Val Leu Phe Leu His Ile Lys Asn Leu Pro Ala Gln Ala Ala Asp Thr
            20                  25                  30

Cys Pro Glu Val Lys Val Val Gly Leu Glu Gly Ser Asp Lys Leu Thr
        35                  40                  45

Ile Leu Arg Gly Cys Pro Gly Leu Pro Gly Ala Pro Gly Pro Lys Gly
    50                  55                  60

Glu Ala Gly Val Ile Gly Glu Arg Gly Glu Arg Gly Leu Pro Gly Ala
65                  70                  75                  80

Pro Gly Lys Ala Gly Pro Val Gly Pro Lys Gly Asp Arg Gly Glu Lys
                85                  90                  95

Gly Met Arg Gly Glu Lys Gly Asp Ala Gly Gln Ser Gln Ser Cys Ala
            100                 105                 110

Thr Gly Pro Arg Asn Cys Lys Asp Leu Leu Asp Arg Gly Tyr Phe Leu
        115                 120                 125

Ser Gly Trp His Asn Ile Tyr Leu Pro Asp Cys Arg Pro Leu Thr Val
    130                 135                 140

Leu Cys Asp Met Asp Thr Asp Gly Gly Gly Trp Thr Val Phe Gln Arg
145                 150                 155                 160

Arg Met Asp Gly Ser Val Asp Phe Tyr Arg Asp Trp Ala Ala Tyr Lys
                165                 170                 175

Gln Gly Phe Gly Ser Gln Leu Gly Glu Phe Trp Leu Gly Asn Asp Asn
            180                 185                 190

Ile His Ala Leu Thr Ala Gln Gly Ser Ser Glu Leu Arg Val Asp Leu
        195                 200                 205

Val Asp Phe Glu Gly Asn His Gln Phe Ala Lys Tyr Lys Ser Phe Lys
    210                 215                 220

Val Ala Asp Glu Ala Glu Lys Tyr Lys Leu Val Leu Gly Ala Phe Val
225                 230                 235                 240

Gly Gly Ser Ala Gly Asn Ser Leu Thr Gly His Asn Asn Asn Phe Phe
                245                 250                 255

Ser Thr Lys Asp Gln Asp Asn Asp Val Ser Ser Ser Asn Cys Ala Glu
            260                 265                 270

Lys Phe Gln Gly Ala Trp Trp Tyr Ala Asp Cys His Ala Ser Ser Leu
        275                 280                 285

Asn Gly Leu Tyr Leu Met Gly Pro His Glu Ser Tyr Ala Asn Gly Ile
    290                 295                 300

Asn Trp Ser Ala Ala Lys Gly Tyr Lys Tyr Ser Tyr Lys Val Ser Glu
305                 310                 315                 320

Met Lys Val Arg Pro Ala
                325

<210> SEQ ID NO 3
<211> LENGTH: 400
<212> TYPE: DNA
<213> ORGANISM: Homo sapiens

<400> SEQUENCE: 3

```
accagaagag atggagctgg acagagctgt gggggtcctg ggcgctgcca ccctgctgct      60
ctctttcctg ggcatggcct gggctctcca ggcggcagac acctgtccag aggtgaagat     120
ggtgggcctg gagggctctg acaagctcac cattctccga ggctgtccgg ggctgcctgg     180
ggcccctggg cccaagggag aggcaggcac caatggaaag agaggagaac gtggcccccc     240
tggacctcct gggaaggcag gaccacctgg gcccaacgga gcacctgggg agccccagcc     300
gtgcctgaca ggtgactgac caccccacac tcctcccac ggcttgtggc tgcccttggc      360
tggaagtcca gggtcatacg acgccattgc cagaatgaag                           400
```

<210> SEQ ID NO 4
<211> LENGTH: 102
<212> TYPE: PRT
<213> ORGANISM: Homo sapiens

<400> SEQUENCE: 4

```
Met Glu Leu Asp Arg Ala Val Gly Val Leu Gly Ala Ala Thr Leu Leu
  1               5                  10                  15
Leu Ser Phe Leu Gly Met Ala Trp Ala Leu Gln Ala Ala Asp Thr Cys
             20                  25                  30
Pro Glu Val Lys Met Val Gly Leu Glu Gly Ser Asp Lys Leu Thr Ile
         35                  40                  45
Leu Arg Gly Cys Pro Gly Leu Pro Gly Ala Pro Gly Pro Lys Gly Glu
     50                  55                  60
Ala Gly Thr Asn Gly Lys Arg Gly Glu Arg Gly Pro Pro Gly Pro Pro
 65                  70                  75                  80
Gly Lys Ala Gly Pro Pro Gly Pro Asn Gly Ala Pro Gly Glu Pro Gln
                 85                  90                  95
Pro Cys Leu Thr Gly Asp
            100
```

<210> SEQ ID NO 5
<211> LENGTH: 900
<212> TYPE: DNA
<213> ORGANISM: Homo sapiens

<400> SEQUENCE: 5

```
atggatctac tgtggatcct gccctccctg tggcttctcc tgcttggggg gcctgcctgc      60
ctgaagaccc aggaacaccc cagctgccca ggacccaggg aactggaagc agcaaagtt      120
gtcctcctgc ccagttgtcc cggagctcca ggaagtcctg gggagaaggg agccccaggt     180
cctcaagggc cacctggacc accaggcaag atgggcccca gggtgagcc aggagatcca      240
gtgaacctgc tccggtgcca ggaaggcccc agaaactgcc gggagctgtt gagccagggc     300
gccaccttga gcggctggta ccatctgtgc ctacctgagg caggccctcccagtcttt       360
tgtgacatgg acaccgaggg gggcggctgg ctggtgtttc agaggcgcca ggatggttct     420
gtggatttct tccgctcttg gtcctcctac agagcaggtt ttgggaacca agagtctgaa     480
ttctggctgg gaaatgagaa tttgcaccag cttactctcc agggtaactg ggagctgcgg     540
gtagagctgg aagactttaa tggtaatcgt actttcgccc actatgcgac cttccgcctc     600
ctcggtgagg tagaccacta ccagctggca ctgggcaagt tctcagaggg cactgcaggg     660
gattccctga gcctccacag tgggaggccc tttaccacct atgacgctga ccacgattca     720
agcaacagca actgtgcagt gattgtccac ggtgcctggt ggtatgcatc ctgttaccga     780
```

```
tcaaatctca atggtcgcta tgcagtgtct gaggctgccg cccacaaata tggcattgac    840
tgggcctcag gccgtggtgt gggccacccc taccgcaggg ttcggatgat gcttcgttaa    900
```

<210> SEQ ID NO 6
<211> LENGTH: 299
<212> TYPE: PRT
<213> ORGANISM: Homo sapiens

<400> SEQUENCE: 6

```
Met Asp Leu Leu Trp Ile Leu Pro Ser Leu Trp Leu Leu Leu Gly
1               5                   10                  15

Gly Pro Ala Cys Leu Lys Thr Gln Glu His Pro Ser Cys Pro Gly
                20                  25                  30

Arg Glu Leu Glu Ala Ser Lys Val Val Leu Leu Pro Ser Cys Pro Gly
                35                  40                  45

Ala Pro Gly Ser Pro Gly Glu Lys Gly Ala Pro Gly Pro Gln Gly Pro
            50                  55                  60

Pro Gly Pro Pro Gly Lys Met Gly Pro Lys Gly Glu Pro Gly Asp Pro
65                  70                  75                  80

Val Asn Leu Leu Arg Cys Gln Glu Gly Pro Arg Asn Cys Arg Glu Leu
                85                  90                  95

Leu Ser Gln Gly Ala Thr Leu Ser Gly Trp Tyr His Leu Cys Leu Pro
                100                 105                 110

Glu Gly Arg Ala Leu Pro Val Phe Cys Asp Met Asp Thr Glu Gly Gly
                115                 120                 125

Gly Trp Leu Val Phe Gln Arg Arg Gln Asp Gly Ser Val Asp Phe Phe
            130                 135                 140

Arg Ser Trp Ser Ser Tyr Arg Ala Gly Phe Gly Asn Gln Glu Ser Glu
145                 150                 155                 160

Phe Trp Leu Gly Asn Glu Asn Leu His Gln Leu Thr Leu Gln Gly Asn
                165                 170                 175

Trp Glu Leu Arg Val Glu Leu Glu Asp Phe Asn Gly Asn Arg Thr Phe
                180                 185                 190

Ala His Tyr Ala Thr Phe Arg Leu Leu Gly Glu Val Asp His Tyr Gln
                195                 200                 205

Leu Ala Leu Gly Lys Phe Ser Glu Gly Thr Ala Gly Asp Ser Leu Ser
            210                 215                 220

Leu His Ser Gly Arg Pro Phe Thr Thr Tyr Asp Ala Asp His Asp Ser
225                 230                 235                 240

Ser Asn Ser Asn Cys Ala Val Ile Val His Gly Ala Trp Trp Tyr Ala
                245                 250                 255

Ser Cys Tyr Arg Ser Asn Leu Asn Gly Arg Tyr Ala Val Ser Glu Ala
                260                 265                 270

Ala Ala His Lys Tyr Gly Ile Asp Trp Ala Ser Gly Arg Gly Val Gly
            275                 280                 285

His Pro Tyr Arg Arg Val Arg Met Met Leu Arg
            290                 295
```

<210> SEQ ID NO 7
<211> LENGTH: 19
<212> TYPE: DNA
<213> ORGANISM: Homo sapiens

<400> SEQUENCE: 7

```
cctggatgcg caaagttca                                                  19
```

```
<210> SEQ ID NO 8
<211> LENGTH: 15
<212> TYPE: DNA
<213> ORGANISM: Homo sapiens

<400> SEQUENCE: 8
gcttgggctc cccgc                                                    15

<210> SEQ ID NO 9
<211> LENGTH: 20
<212> TYPE: DNA
<213> ORGANISM: Homo sapiens

<400> SEQUENCE: 9
gatggtcatg atggttcctg                                               20

<210> SEQ ID NO 10
<211> LENGTH: 20
<212> TYPE: DNA
<213> ORGANISM: Homo sapiens

<400> SEQUENCE: 10
ggtattgttt ggcattcacg                                               20

<210> SEQ ID NO 11
<211> LENGTH: 24
<212> TYPE: DNA
<213> ORGANISM: Homo sapiens

<400> SEQUENCE: 11
gacaggatgc agaaggagat tact                                          24

<210> SEQ ID NO 12
<211> LENGTH: 21
<212> TYPE: DNA
<213> ORGANISM: Homo sapiens

<400> SEQUENCE: 12
tgatccacat ctgctggaag g                                             21

<210> SEQ ID NO 13
<211> LENGTH: 29
<212> TYPE: DNA
<213> ORGANISM: Homo sapiens

<400> SEQUENCE: 13
atcattgctc ctcctgagcg caagtactc                                     29

<210> SEQ ID NO 14
<211> LENGTH: 20
<212> TYPE: DNA
<213> ORGANISM: Homo sapiens

<400> SEQUENCE: 14
ccacatcgct cagacaccat                                               20

<210> SEQ ID NO 15
<211> LENGTH: 16
<212> TYPE: DNA
<213> ORGANISM: Homo sapiens

<400> SEQUENCE: 15
```

```
ccaggcgccc aatacg                                                    16

<210> SEQ ID NO 16
<211> LENGTH: 28
<212> TYPE: DNA
<213> ORGANISM: Homo sapiens

<400> SEQUENCE: 16
aaggtgaagg tcggagtcaa cggatttg                                       28
```